(12) United States Patent
Li et al.

(10) Patent No.: US 8,138,391 B1
(45) Date of Patent: Mar. 20, 2012

(54) ***OR* GENE AND ITS USE IN MANIPULATING CAROTENOID CONTENT AND COMPOSITION IN PLANTS AND OTHER ORGANISMS**

(75) Inventors: Li Li, Ithaca, NY (US); David F. Garvin, Roseville, MN (US); Shan Lu, Ithaca, NY (US); Julia Vrebalov, Ithaca, NY (US); Diana M. O'Halloran, Binghamton, NY (US)

(73) Assignees: The United States of America as represented by the Secretary of Agriculture, Washinton, DC (US); Boyce Thompson Institute Inc., Ithaca, NY (US); Cornell University, Ithaca, NY (US)

( * ) Notice: Subject to any disclaimer, the term of this patent is extended or adjusted under 35 U.S.C. 154(b) by 1162 days.

(21) Appl. No.: 11/296,025

(22) Filed: Dec. 7, 2005

(51) Int. Cl.
*C12N 15/05* (2006.01)
*C12N 15/29* (2006.01)
*C12N 15/82* (2006.01)

(52) U.S. Cl. ........ 800/282; 800/306; 800/312; 800/314; 800/317.4; 800/320; 800/320.1; 800/320.2; 800/320.3; 536/23.1; 435/419

(58) Field of Classification Search .................. None
See application file for complete search history.

(56) References Cited

OTHER PUBLICATIONS

Li, L. et al. Molecular General Genomics, 2003; vol. 270, pp. 132-138.*

Lu, S. et al. The Plant Cell, 2006; vol. 18, pp. 3594-3605.*

* cited by examiner

*Primary Examiner* — Russell Kallis
(74) *Attorney, Agent, or Firm* — John D. Fado; Evelyn M. Rabin

(57) ABSTRACT

The cauliflower (*Brassica oleracea* L. var. *botrytis*) Or gene is a semi-dominant, single-locus mutation. It induces the accumulation of high levels of beta-carotene in various tissues that are normally devoid of carotenoids, turning them orange. Using a map-based cloning strategy, we identified a single candidate gene representing Or and successfully verified its identity by phenotypic complementation in the wild type cauliflower. The Or gene encodes a plastid membrane protein containing the DnaJ zinc figure domain. A likely gain-of-function mutation from a 4.3-kb retrotransposon insertion in the Or allele confers the orange phenotype in the mutant. Southern blot analysis revealed that Or is a single-copy sequence in the cauliflower genome. High level of expression of the Or gene and the protein was found in very young leaves, curds, and flowers at comparable abundance between wild type and the Or mutant. Or likely functions in regulating the differentiation of some non-photosynthetic plastids into chromoplasts, which provide the deposition "sink" for carotenoid accumulation. Or orthologs with high degree of sequence homology were found in many other higher plants, including *Arabidopsis*, tomato, maize, and rice. Successful phenotypic complementation of Or in *Arabidopsis* provides strong evidence that Or can work across species to enhance carotenoid accumulation in other important crops.

22 Claims, 24 Drawing Sheets

(4 of 24 Drawing Sheet(s) Filed in Color)

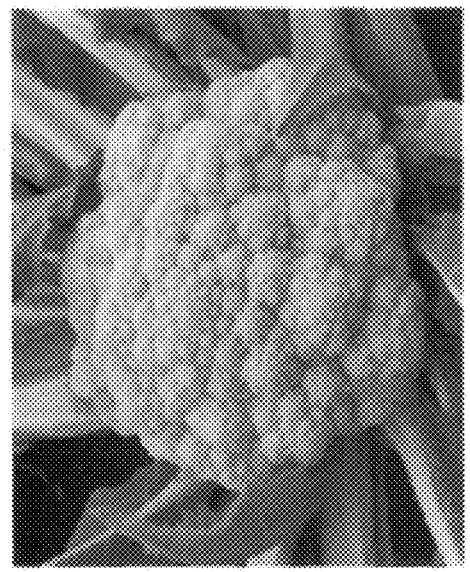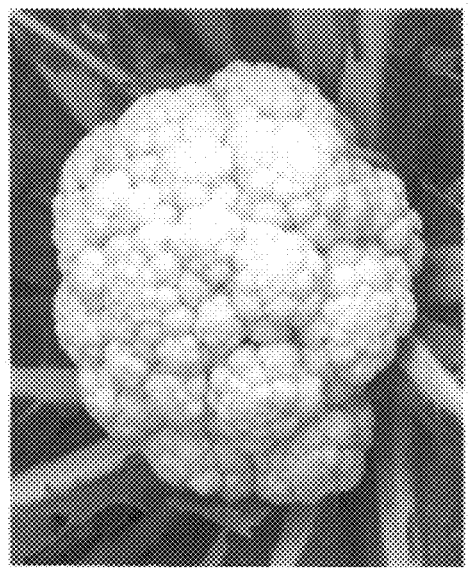
FIG. 1

```
SEQ ID NO: 1
cDNA      :                                                                                                    :   0
P-Cluster : AGTACTTCCATTATTATGCAATATATACTATATAATGCTCTCTTAGTAACCGGTTAATGAAAGATAAAAATATCTCTTCTTCTTCTTCTTGATTAACAACTA : 100 cDNA      :                                                                                                    :   0
P-Cluster : CCATCAATCTACTTTCATCTCTACCACCTTGTCCCTCCGACGCCCGTTACAATACGATCATCACTAATTCTCCATTGTGTTTTGTATTTATAGATTTTTTT : 200 cDNA      :                                                                                                    :   0
P-Cluster : CTATAATCAGTATCATTTTTCATAAATTATCACCTCATTCATATTCACATTTATCACTGAACTACCATCACCATAGCCATGAAATCTACAAACGGCGTTA : 300 cDNA      :                                                                                                    :   0
P-Cluster : CGGTCGAGGGCGCCCTCATTGTATCGTAAGTTTTTGGTTATACTATACTATTTGGACAATATGTACTATATTATTCCTTTGTTACTATTTTATTTCATA : 400 cDNA      :                                                                                                    :   0
P-Cluster : TGCTTTCATATTATGTACTACATGCATATTTTGATATTTGGGTTAGAATTATATTTTTTTTTAAGTTTAGTGATTAGTGTTTTGGGTTAGTTTATGGA : 500 cDNA      :                                                                                                    :   0
P-Cluster : AGTTTGGACTGACGTTGAGGTAAGCATTACCTCATTCATGCAATCATAAGCATTTCAAAATTTGAAAAATATGTACTATGTTATTCGTTTGTTACTAT : 600 cDNA      :                                                                                                    :   0
P-Cluster : TTTATTTGATAATGCTTCATATTATGTACTGTGTGCATATTTTGATATTAGGGCTAGGATTATATATAGTAGTGATTATATAGTGTTTTGGGTTAGTGTTTTATGAAAAA : 700 cDNA      :                                                                                                    :   0
P-Cluster : TTTAGATTGACAGAGAATAAGCATTACTTCCACTATTATTATTAATTTCATTAATATGAACTATACCATATGAAGAATGTTCTATTCTATTACTCTGCTTAT : 800 cDNA      :                                                                                                    :   0
P-Cluster : CTTCTTCCATAACATTATATCTTTCTCCGATCATCGCAATCATATTAATCTTTGTATGAAAGATGACTGTTCTTCTTTTGGATTGACAACCTCTGTTTCATT : 900 cDNA      :                                                                                                    :   0
P-Cluster : TTTAATCACTCTTGCCGTAGTCATCATCTTCGTAGTCTCCGCCACCGGTGCGATAACCAATATCACCGTTCTGATAACCACTACCGCCGCGACCATA : 1000
```

FIG. 3

```
cDNA          : ------------------------------------------------------------ :    -
P-Cluster     : CCGCAATAATCACCCAAATATTGATTACAATTTTTTTTCTTTGACTGGCAACTGCCAACTGGTTCAAAAAAGGACAAAACCGAGAAATATAGCACA : 1100 cDNA          : ------------------------------------------------------------ :    -
P-Cluster     : AATGCTATGAGATCTAATAACTTCAAATTAGTGACATATTCTTAATTGTTGGTGAAATATGACTGTTCACAAATAAGCCCTGTAATATTGGCACATG : 1200 cDNA          : ------------------------------------------------------------ :    -
P-Cluster     : GCAAAAGAAAACTACCAAGTATATTTGGGTCAGCATGTTATCATCTTATACTAATAAGCGCAATGTAAAGGCCTTTGCACCAAGGAAAATGTTTACA : 1300 cDNA          : ------------------------------------------------------------ :    -
P-Cluster     : AAACCCACCAAAACATTTAATATATAATTCGACACCGCCCACTTGTATTTCTTTGTAAACACCTTTAAAGATAAGCATGCATGGATTATCCATAACAA : 1400 cDNA          : ------------------------------------------------------------ :    -
P-Cluster     : AAAAAATTCCCAAGTCTGGAAAAAAAAAATATCCTGCCACCACAGAAGTTTATGAAAAACGAAATTTATTTAATTAAACTAAACACTAAAAACAAGTG : 1500 cDNA          : ------------------------------------------------------------ :    -
P-Cluster     : TAAAATAAACAATAACAACCAGTAAATCTCGCCACGCACCTACAAAAACTACAGTTCGTAATAGAGTGGTGTCTCTCTCTCTCTCGGTCTCGATT : 1600 cDNA          : ------------------------------------------------------------ :    -
P-Cluster     : TCTGATTTCTGATTCCTCACTGTACGACCAAACTAACCACACTGACAGAACACATAAAAGAACAGGCAAACTAATTGATCCGCTGAAGATCTCG : 1700
                                                                                                SEQ ID NO: 2
cDNA          : ------ATGTCTGTTGGGTAGGATCTTGTCGTTCCTACCCACCCGGATCGCGTACGGTTCCGCGTCTCTTTCAGTGTCCAAGCGTGTCTTCACCAGGGAGAAA :   95
P-Cluster     : AAACCATGTCTCTTGTTGGGTAGGATCTTGTCGTTCCTACCCACCCGGGATCGCTTCCGCGTCCTTTCGCGTCTTTCAGTGTCAAAGCGTCTTCTTCACCAGGAGAAA : 1800
                     |― Exon 1 cDNA          : CCGAAGGCCTGAGATGGGCTTTCAGGGCCTTGGACTCACAGCTCTTCCTCCCTGATTCGGACAAATTCGGTCGCGG---------------------- :  179
P-Cluster     : CCGAAGGCTGAGATGGGCTTTCACGGGCTTGGACTCACAGCTCTTCGTCCCTGATTCGGACAAATTCGGTCGCGGGTATTCAAATTTAAGCT : 1900
                                                                                          Exon 1 ―| cDNA          : ------------------------------------------------------------ :    -
P-Cluster     : CTTTAACCGATGTTTTGTTATGCCACCCGTAAAGTTGAACCCGTAAAGTTACAGACTTTGGAGTTTAATCGTATTTAAGTTGTATTTGATTATTTTT : 2000 cDNA          : -----CTTTTGTATCATAGAAGGACCTGAAACAGTACAGGACTTTGGCAAAATGCTAATTACAGAGATTCAAGACATTAGAAGCGTGAAACAA :  272
P-Cluster     : GGTGCAGCTTTTGTATCATAGAAGGACCTGAAACAGTACAGGACTTTGGCAAAATGCCAAAATGCCTAATTACAGAGATTCAAGAGATTAGAAGCCGTCGAAACAA : 2100
                     |― Exon 2
```

Fig. 3 (cont.)

```
                         Exon 2 →|                                                                    |→
cDNA      :                                                          TTACTTTCTTAAGTGGAAACCTTTAGTTTCTTAAACTGTCTTCCTCGTTAACTATCTGTTAATACAGGT : 298
P-Cluster :                                                          TTACTTTCTTAAGTGGAAACCTTTAGTTTCTTAAACTGTCTTCCTCGTTAACTATCTGTTAATACAGGT : 2200
                         Exon 3                                                    (← LTR Retrotransposon →
cDNA      :               GGAGGCTAAGAATAGAACACACGGATTAGAACAACAGAGAGCTTGGAATCATAGAACGAAGAGCAAGAACACGAAGCTAAAGTGGCAGAATCCGAACTTGGTATG : 370
P-Cluster :               GGAGGCTAAGAATAGAACACACGGATTAGAACAACAGAGAGCTTGGAATCATAGAACGAAGAGCAAGAACACGAAGCTAAAGTGGCAGAATCCGAACTTGGTATG : 2300 cDNA      :                                                                                                                  : -
P-Cluster : ATCGTATGAACACAAACTTAATAAATAAAAACTTTGCTTGTCTTATTAATCTTCTATTAATCTTCTATTCTCTTTTTTCTTAATTAAAAACTCTCTACACTTAGG : 2400 cDNA      :                                                                                                                  : -
P-Cluster : CTTTCTTATATAGGCAATAGAAATCTTAACTTACCTATTACCTATTACAGATATTAATAATCTAGGAATATCTTAACTTAGCTTATCTTATCCTAAATCTATTTGTATAAGT : 2500 cDNA      :                                                                                                                  : -
P-Cluster : TATTCCCTCGTTCCTTTTTGAATAACTTATTACTCAAGTAACTTCTCCCCTTCTTAAGCTTATCCAACATTCTCAAACCATTTTCACTTAGGTTTG : 2600 cDNA      :                                                                                                                  : -
P-Cluster : AACTTCAATCATCATGACCTCATTCCTTCCTAGAATTTGATCTTGGCCAATGCTTTAGTTAGTTAGGATGTCTCGTCTGCTCTGTCCCGGTACATGTTCCACATCA : 2700 cDNA      :                                                                                                                  : -
P-Cluster : ATGAGATTGCGCTCAACACATTCCCTAATGAAGTGAAACCTCTTGCTTGCTTCGGTGAAAGACTGGATTCTTTGCAAGAGATATAGCTG : 2800 cDNA      :                                                                                                                  : -
P-Cluster : ACTTGTTTATCGACTAGAATCAGTGTCTCTTCCGTCTCTCACCTCCGTTACTTCACTCAAGAGTTCTTGTAACCAGATAGCCTGTTTAGCAGCCTCCGTTGC : 2900 cDNA      :                                                                                                                  : -
P-Cluster : AGCCATGAACTCGGCTTCGCAGGATGACAACGCCACTGTGTCTTGTGTTTCTGAGAGCACCAAGTGTGTGTTTCCTAGACAGAACAGGTGACCTGTT : 3000 cDNA      :                                                                                                                  : -
P-Cluster : GTGCTCCTTCCATCGTCCGGATCAGTATTGTGACTACTGTGCTGTACCCTACAAGTTTCTGTGTACTTCCACGTTAAACTCTAGAACTCTAGAACTCTAGACATGCCCGAGAG : 3100
```

Fig. 3 (cont.)

```
cDNA         : ----------------------------------------------------------------------  -
P-Cluster    : TTCCTTGTGTAGATATCTTAAAACTTGCTTAAACGCATTCCCGTGAGACTCTCTCGGTGATTGCATATATCTACTTAGGATCCCAACTGAGTATGCCATGTC : 3200 cDNA         : ----------------------------------------------------------------------  -
P-Cluster    : TGGTCTAGTGTGCATTAAGTACCCTTAAGCACCCAATCTTTCTTTCTTTGATATTGAGTTGCATCAATCTCTGGTTCATCCAGTGCCTTTGAGAATTGTAGACCG : 3300 cDNA         : ----------------------------------------------------------------------  -
P-Cluster    : AACTCCATTGGAATACAATTTGATTGCAATCGGCCATACGGCCATATACCTGATTCTTCTTCCATGATCCGTTTGCATAGGCTTCTTGTTGATTGTGATCCCTCTAGTGC : 3400 cDNA         : ----------------------------------------------------------------------  -
P-Cluster    : TCTGCTTTACTTCAATGCCTAGATGCCTAGATAATAGGTTAGCAACCCGAGATCAGACATTTCAAACTTGTGTGACATCGCTGCTTGAACTCTTTGATGATCTTTGT : 3500 cDNA         : ----------------------------------------------------------------------  -
P-Cluster    : TGAATTCCTGTAACAAAGAGATCATCCACATATATTGCGATAATCAGAGAGCTTATCTCCTTCTCTTCTGTAGACCGAGCTTTCTTCTTCATGCACTTC : 3600 cDNA         : ----------------------------------------------------------------------  -
P-Cluster    : TTGAACCGCAAACTCTTAAGAACGACGGATCGAGTGTATTCCAAGCGCGGCGGATCGAGTTAGTATTCCAAGGCGCTTGCCTTAGACCATATAGTGCCTTTGAGAGTTGAAAACTTTAT : 3700 cDNA         : ----------------------------------------------------------------------  -
P-Cluster    : GTTCTTCTCCCTTTTTTCAAACCCTTCAGGTGAGTTACATAGACTTCTTCATTCAATTCTCCATGTAAGAATGCCGTCTTGACGTCTAGGTGGTGAAG : 3800 cDNA         : ----------------------------------------------------------------------  -
P-Cluster    : TTCCCATCCTTTGCAGAGAAGCTAAGCTGATTAAGAGTCGAATGGACTCTATACGAGCTACTGGAGCAAACACTTCTTCAAAATCAATTCCATGCTCTTGT : 3900 cDNA         : ----------------------------------------------------------------------  -
P-Cluster    : ACATATCCCTTTGCTACAAGTCTTGCTTTGAATTTGTTGATTGATCCATCTGCGTTCCTTTTGATCTTGAAAATCCACTTAAGACCAATGACTTAACTC : 4000 cDNA         : ----------------------------------------------------------------------  -
P-Cluster    : CGTGGCTTATCTACCAACTTCCATGTCTGGTTTCTTCGTTGATAGAGTCAATCTTCGCATGCTTTTGTCCATCGAACATGTATCTTAGCTTCTTG : 4100 cDNA         : ----------------------------------------------------------------------  -
P-Cluster    : GTATGTTGATGGTTCATCGTTGATTGAACACAGGAGTAGTTCGCATTCTATCTCGGCCGAGTAGTAGAATGAATCTTCTAGGTGTTTGGGAAGTTTACTTCT : 4200
```

Fig. 3 (cont.)

```
cDNA        : ------------------------------------------------------------ :
P-Cluster   : CTAGATGATCTTCTTGGTTCGACGTGATCTACCTCGGGGGTTGGCTCTGTTGTTCTTCTGTTCTTCAGTCTGCAATATTTCTTCCTGATGTG : 4300 cDNA        : ------------------------------------------------------------ :
P-Cluster   : AACCTATGACAAACGGACCGTTACCCTCGTCGTCTATGCTTGATCCCCACGTCGTTGAACTTGCCAGAGATTCTTCTTGTTCCTTTATCGTTTCATTCCA : 4400 cDNA        : ------------------------------------------------------------ :
P-Cluster   : GTTCCAGCATGCTTTCTCATCGAACTTCACGTCTCGAACTTCTCGACTAACCACACAATCCTTCGTGCTAGGATTATATAAGCGGTAAGCTTTCGACCCTGGTTCTATA : 4500 cDNA        : ------------------------------------------------------------ :
P-Cluster   : CCAAGGTGAACCAGTGTCTGTGATCTGTGTCATGCGAGTTCTTCAAAAGGGCAGCATCGAGTTTGGCATATGCCAAACAGCCAAAGACTCTGATGTGTCCAA : 4600 cDNA        : ------------------------------------------------------------ :
P-Cluster   : TGCTCGGCTTTCTTCCTTTGAAACTCTCATAAGGAGAGTTTGATTCTTCAAAGCTCTAGTTGGAACTCGATTGATCAGATACGTTGCATGTCGAACAGCCTC : 4700 cDNA        : ------------------------------------------------------------ :
P-Cluster   : TCCCCACATATAATTTGGAACATTCATCGCTTTTAACATACTGCGCGTCATCTCCGGTTTCTTCTTTCGACAACGCCGTTTGCTGTGGC : 4800 cDNA        : ------------------------------------------------------------ :
P-Cluster   : GTATATGGCGCAGTTAGATGTCTCCTAATACCATTGTTGTTGCAGTAATCTTGAAGTAAACTCTCTGTGCGAAGTGTTA : 4900 cDNA        : ------------------------------------------------------------ :
P-Cluster   : CTATTACTTTATTGACCTCCTTCCTCTACAAGAGCTTTAAAGGTCTTGAATTTCTCAAAGACTTCACTTTTTTCTTGAGTAAAATAGACCACATGTATCT : 5000 cDNA        : ------------------------------------------------------------ :
P-Cluster   : TGTGTTGTCATCAATTATGACAATATGTGTCCAGTGTTGAAGGAGAGATTGGACCGCAGAGGTGCAACAACTCTAATACCTGC : 5100 cDNA        : ------------------------------------------------------------ :
P-Cluster   : GACGACCTATGTGGTGTTGCAGAGGGAAAACTATTTCGAGTCTGTTCCCAACGAGACTCACAAAGCTTCTTCTTCGTTGATCTCAGGTAGTC : 5200 cDNA        : ------------------------------------------------------------ :
```

Fig. 3 (cont.)

```
cDNA            : ----------------------------------------------------------  :
P-Cluster       : CTCGAACCATCTCGAGTTTTGCCATGTCTTTTATCGTCTTGAAGTTGATATGGCCAAGGCGTGCCATCTCCACGGTTCTTCATTAATCTTTGTGAG : 5300 cDNA            : ----------------------------------------------------------  :
P-Cluster       : AAGGCAGCTTGGTTTTCCAACTTGTTGAGTGATGATACCTTGTAGAGACGATTAGTGATTAGTTGATCTTAAGACTTTACAAGTAACCTCCGCTTGGATCTCTCAAAGTC : 5400 cDNA            : ----------------------------------------------------------  :
P-Cluster       : AGATAGTTATCTTTCATTCTTACATCACAGCCTTGTCAGTTGCTTGGCCTAGCTCAGTTGCTTCTTAACTCTGTATATAATATATATTAGTTA : 5500 cDNA            : ----------------------------------------------------------  :
P-Cluster       : GAAGCTTTTGCTCTCCCGTCTTTGCTTGCTTTCAAAGATAATTGAGCCTTTGCCATTGATTTTCACACATGATCATCACCAAACTTAACTCTTCCCTTGATACT : 5600 cDNA            : ----------------------------------------------------------  :
P-Cluster       : TTCATTGAGTTCGGAGAAGAGCTCTTGTCTCCTGTCATATGATTACTAGCACCGTTGTCAAGATACCAATTACCATCATCAGTTTTGTTTTGCTCAAGT : 5700 cDNA            : ----------------------------------------------------------  :
P-Cluster       : TTCTTTTGGCATCACGCTTTCTTCATTCAAAAACACAACTTCATGCATGTATAATGCTGCTTCAGCTACTTCTGTCTCTGCTTTGTTGAGTTGATGATCAT : 5800 cDNA            : ----------------------------------------------------------  :
P-Cluster       : CATTCTCTCGGGACAGAGGCAAAGTGACCCTTCTTGTGGCAGTGAAAGCACTCGATTGAGAGTAATCCTTCTCTCTTTATTTCTCTCACCTCC : 5900 cDNA            : ----------------------------------------------------------  :
P-Cluster       : GTTGCTACTACCACGCCCCCTTCCTCTGTTCCCACGACCCCCTATTGGAACCTCGTCCTCTGCCTTTGGTTCCATGATGATCGGAGTAGAGAGGAGCTTGCCATTA : 6000 cDNA            : ----------------------------------------------------------  :
P-Cluster       : TCTTCAAGTTTCTCCTGCCATTCTCTCCTCTTCCTCCACGGCAGCGGTTCCTCAAATGCTTTGAGGCGACCTACCACCATCTTCGTACCTTGTGTTGTTAGGT : 6100 cDNA            : ----------------------------------------------------------  :
P-Cluster       : CAAGAACTTGTTCTAGTGTTGCTGAGAGCTGAAGAAATTTACTTGGCAGACATGATAGAAACTTCTTTACTAGTTTTGCTTCCTCCTATCGTATGGCCGAG : 6200 cDNA            : ----------------------------------------------------------  :
P-Cluster       : TGATGCAACTGTTCCTGCAAACTCTGATAATTTTCCGGAGAACGTATCTATCGAATCAGTATCTTTCATTCTCAGATGATCGAACTCAATCATCAGTGTG : 6300
```

```
P-Cluster   : GTTTATTGAAATTTATTGGTTAAGTTGCGGGAAAAATCGTTAATAACCAAAAAAAACAATTCATTAATAATATCAGTATTTAATATGTTTTTGAAACCAG : 7400
                                                                                            |← Exon 5
cDNA        : -------------------------------------------------------------------------------GTAGAGCTGAGAGCTAGGTATAGGGGCACATCATATAAAG :  538
P-Cluster   : AGGGTGTATGAGTATTCTTTGCTTTATGTAATAAAGTTTTGATTTGTAACTTCTGCAGCTAGAGCTGAGAGCTAGGTATAGGGGCACATCATATAAAG : 7500
                                                                Exon 5 →|
cDNA        : ATTTCATTCAAAGCCTTCATCTACCTATGCAATTGAG---------------------------------------------------------- :  575
P-Cluster   : ATTTCATTCAAAGCCTTCATCTACCTATGCAATTGAGGTTTAGTATCTCTCTTTATATACATTTGCAACTTTATAGAAAGGATGCTTAACTCTTGTGT : 7600
                   |← Exon 6
cDNA        : ------TCAAGTAGACCCAATAGTGGGCGTCATTCTCGGAGGAGCTGTTGGTGTGATCTCAGCTTTGATGGTAGTTGAAATTACAACGTGAAGCAGCA :  668
P-Cluster   : TCACCAGTCAAGTAGACCCAATAGTGGGCGTCATTCTCGGAGGAGCTGTTGGTGTGATCTCAGCTTTGATGGTAGTTGAAATTACAACGTGAAGCAGCA : 7700
                                                              Exon 6 →|
cDNA        : AGAGCACAAGAGATGCAAATACTGTCTAGGAAGTGG------------------------------------------------------------- :  704
P-Cluster   : AGAGCACAAGAGATGCAAATACTGTCTAGGAAGTGGTAATTAATGTTTCCTCTTCTGTTCATAAAGAGATTTAAGTTGTTGGTTTTAATAACTTTTCTTA : 7800
                        |← Exon 7
cDNA        : ---------GTATCTAGCATGTGCCGTTGCCTCTAGCACAGTTCTCTTAATTATATCTGAACCAGTCTCAGCTATTGCTGGAGGAACCATTCT :  789
P-Cluster   : TGTAACACACAGGGTATCTAGCATGTGCCGTTGCCTCTAGCACAGTTCTCTTAATTATATCTGAACCAGTCTCAGCTATTGCTGGAGGAACCATTCT : 7900
                                                              Exon 7 →|
cDNA        : GTATCAACATCCAAAACCGAAAGATGTTCAAACTGTTCTGGTGCTGGAAGGT-------------------------------------------- :  842
P-Cluster   : GTATCAACATCCAAAACCGAAAGATGTTCAAACTGTTCTGGTGCTGGAAGGTATAAACCATCAAAAACCATCAAAACCAAAACCTAAAAGCCCAAAACCAAAAAT : 7997
                                                                |← Exon 8
cDNA        : ---------------------------GATGTGTCGGACATGTCTGTGCAGGAATGGCTATGCTAGCAGCAGGATGGCTGGCTATGCCTGTATTGATC :  907
P-Cluster   : GTGGATGTTGAATTGTCTGTGTTTGTTGTTCAGGTCATGTGTCGGACATGTCTGTGCAGGAATGGCTATGCTAGCAGCAGGATGGCTGGCTATGCCTGTATTGATC : 8097
              Exon 8 →|
cDNA        : CCTTCCTT----------------------------------------------------------------------------------------- :  915
P-Cluster   : CCTTCCTTGATTCCTCTCCCCCCCCCACAAAATCTATTGTCATTGTAACTAAAAATGTTAGATTTTTCTTCGTCCTGTAACACTCTCCAGAATTAGAG : 8197 cDNA        : ------------------------------------------------------------------------------------------------- :    -
P-Cluster   : ATATGTACACACAATGACACAAATGAACTTATTACATAATGTTAGATTTTTCTTCGTCCTGTAACACTCTCCAGAATTAGAG : 8297 cDNA        : ------------------------------------------------------------------------------------------------- :    -
P-Cluster   : CCAGAAACGAAACACACTGTTTCTAGGCTATATGTGGCTTAGAGTTGAGTTGAGTACACTACTTAGTAGGTCTGGGCGGTTCGGACCCGTCGGTTCGGTT : 8397
```

Fig. 3 (cont.)

```
cDNA      : ----------------------------------------------------   :
P-Cluster : GATTCGGATTTTGGTGTTATGCTCATAAGTCCCTTTCGGGTTTTATTAATCTTCGAGTCGGGTTTGGTTCGGTTCCTTCCGGAAATGTTTGAAATCGT : 8497 cDNA      : ----------------------------------------------------   :
P-Cluster : CCAAAAATATGTTTTTTAAACCTCAAAAAATGATAAATATTTTTCATAATAGAAATTATTCACAAATCTAATTAAAATTAGTTAAATATATTTAAATT : 8597 cDNA      : ----------------------------------------------------   :
P-Cluster : AACTAAAAAGTATTCAAAATAACAAATAAAACAAACTACAAAAATATTTGAATACTCTAAAATATCTCAACGTATATAAAAACATTAACA : 8697 cDNA      : ----------------------------------------------------   :
P-Cluster : CATTTAACTAATTCAAATATCTTCGGATCCTAGTTTGGATTTCGGTTCGGTTCGTTTATAACCAAACCCAAAATACTAAGCTTATAAGTCTCGTTCG : 8797 cDNA      : ----------------------------------------------------   :
P-Cluster : GATATTTTGTATAACAGTTTGGATCCGGTTTCGGTTTTCCAGTTCGGGTTTAGGTAGGATTGGAGTAAAACGCCCAGGCCTACTAGTTAGTAGCTTA : 8897 cDNA      : ----------------------------------------------------   :
P-Cluster : GTGAGTAAAATTAGGTTCTAAGATGATAATCGCTTCTAAGTAATACTTTTCACTAATTCTCAGCTTACTGATGTTGACACTGTTACTTCTTCAGGCTCCA : 8997 cDNA      : ----------------------------------------------------   :
P-Cluster : AATCTAGTTACTTCCATTGAAACTTCATTAAAACTCATATGAAAAAGTACAGTACAATGGTTTCGGCAGGACATAACCAAATTATACAATCGAAA : 9097 cDNA      : ----------------------------------------------------   :
P-Cluster : GAGACACAAGTCTGTATCCAAACACAGTTAGCCCAAGGAAGGAAGAACTGAGATTATTATTTGAAGGACACAGTTAGTTAGTCCCAGTGCCCATTCT : 9197 cDNA      : ------------   :
P-Cluster : CGCAGCGGTTGTCT : 9211

Note:

cDNA = wild type cDNA sequence starting with ATG of exon 1.
P-Cluster = 9.2 kb Or allele with retrotransposon
```

| | | | |
|---|---|---|---|
| Or-D1 | : ---------- : - | SEQ. ID NO: 4 |
| Or-I | : ---------- : - | SEQ. ID NO: 5 |
| Or-D2 | : ---------- : - | SEQ. ID NO: 6 |
| Wt-or | : AAAAAAAAAAA : 1162 | SEQ. ID NO: 3 |

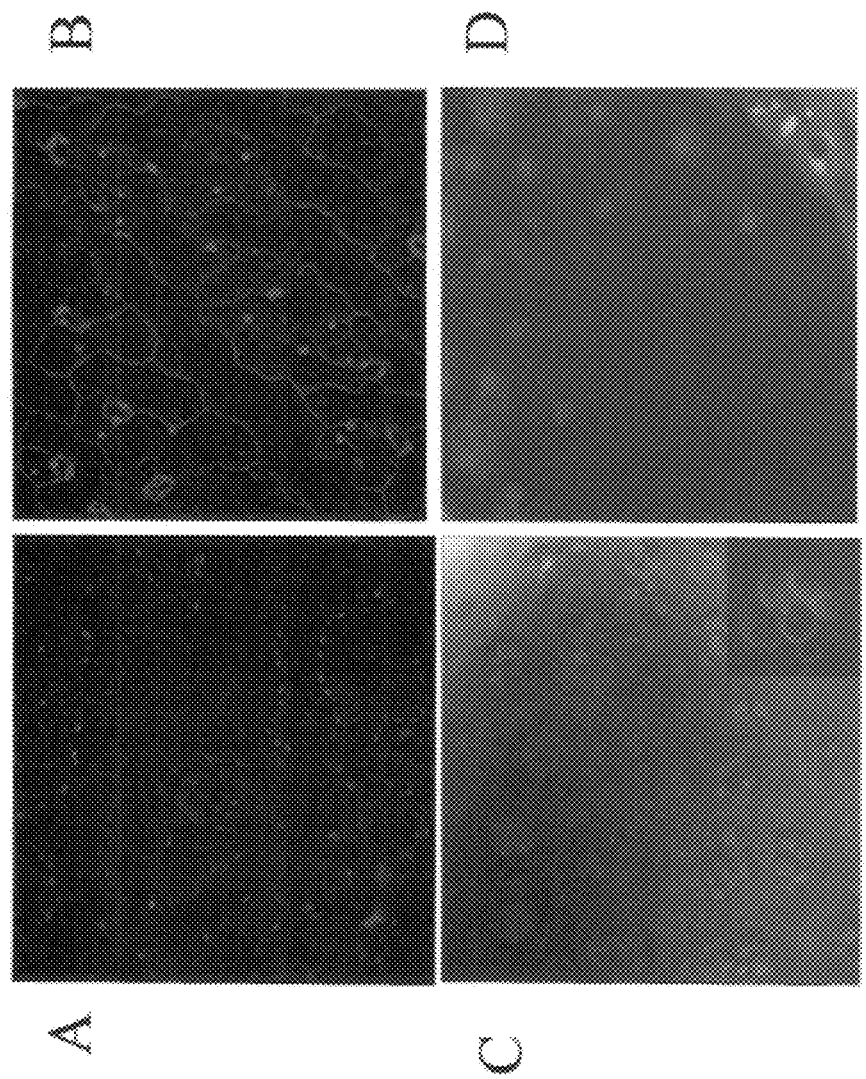
FIG. 10A-D

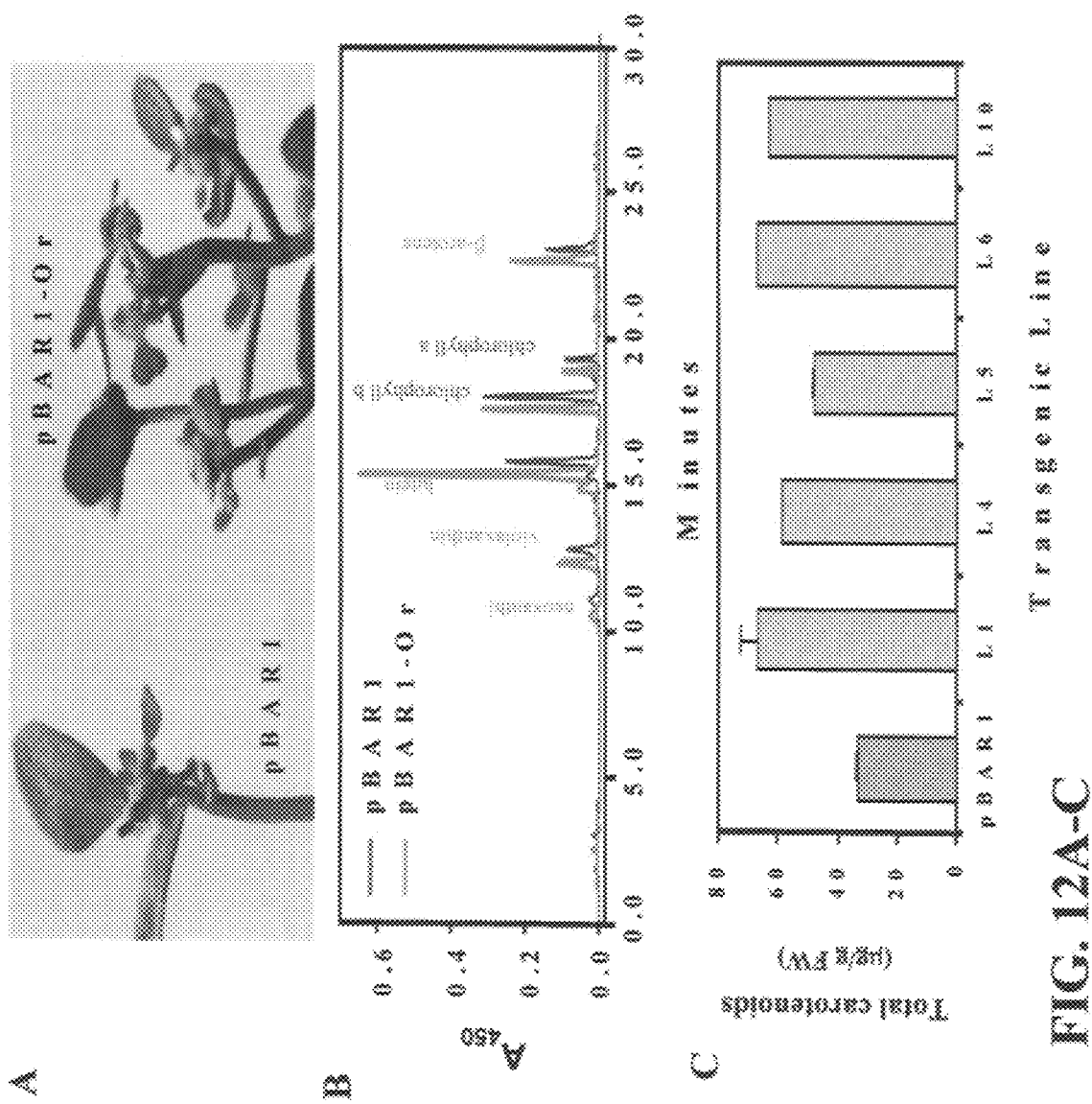
FIG. 12A–C

SEQUENCE LISTING

```
<160> NUMBER OF SEQ ID NOS: 25

<210> SEQ ID NO 1
<211> LENGTH: 9227
<212> TYPE: DNA
<213> ORGANISM: Brassica oleracea

<400> SEQUENCE: 1
agtacttcca ttatttatgc aatatatact ataatgctct tagtaaccgg ttaatgaaag      60
ataaaaatat ctcttcttct tcttcttcga ttaacaacta ccatcaatct actttcatct     120
ctaccacctt gtcctccgac gccgttacaa tacgatcatc actaattctc cattgtgttt     180
tgtatttata gattttttt ctataatcag tatcattttt cataaattat cacctcattc      240
atattcacat ttatcactga actaccatca ccatagccat gaaatctaca aacggcgtta     300
cggtcgaggc gccctcattt gtatcgtaag tttttggtta tactatacta tttggacaat     360
atgtactata ttatttcctt tgttactatt ttatttcata tgcttcatat tatgtactac     420
atgcatattt tgatatttgg gttagaattt atatttttt tttaagttta gtgattagtg     480
ttttgggttt agtttatgga aggtttggac tgacgttgag gtaagcatta cctcattcat     540
gcaatcataa gcatttcaaa atttgaaaaa tatgtactat gttatttcgt ttgttactat     600
tttatttgat aatgcttcat attatgtact gtgtgcatat tttgatatta gggctaggat     660
ttatatagtg attagtgttt tgggtttagt ttatgaaaaa tttagattga cagagaataa     720
gcattacttc cactattatt aatttcatta atatgaacta taccatatga agaatgttct     780
attctattta ctctgcttat cttcttccat aacattatat ctttctccga tcatcgcaat     840
catattaatc tttgtatgaa agatgactgt ttcttttgga ttgacaacct ctgtttcatt     900
tttaatcact cttgccgtag tcatcatctt cgtagtctcc gccaccgccg gtgcgataac     960
caatatcacc gttctgataa ccactaccgc cgcgaccata ccgcaataat caccacaaat    1020
attgattaca attttttttt ctttgactgg caactgccaa ctggttcaaa aaaaggacaa    1080
aaccgagaaa atatagcaca aatgctatga gatctaataa cttcaaaatt agtgacatat    1140
tcttaatttg ttggtgaaat atgactggtt cacaaataag ccctgtaata ttggcacatg    1200
gcaaaaagaa aactaccaag tatatttggg tcagcatgtt atcatcttat actaataagc    1260
gcaattgtaa aaggcctttg caccaaggaa aatgtttaca aaacccacca aaacatttaa    1320
```

```
tataattcga caccgcccac ttatgtattt tcttttgtaa acacctttaa agataagcat    1380
gcatggatta tccataacaa aaaaaattcc caagtctgga aaaaaaaaaa tatcctgcca    1440
ccacaagttt tatgaaaacg aaatttattt aattaaacct accaacacta aaacaagtg    1500 taaaataaac aaatacaaca accagtaaaa tctcgccacg tacaaaaact acagttcgta    1560
atagagtgtg gtggtctctc tctctctctc ggtctcgatt tctgatttct gattcctcac    1620
tgtacgacca aaactaaacc acactgacag acacacataa agaacaggc aaactaattg    1680 atccgctgct gaagatctcg aaaccatgtc ttgtttgggt aggatcttgt ctgtttccta    1740
cccaccggat ccttccggtt cgcgtctttc agtgtcaaag ctgtcttcac cagggagaaa    1800
ccgaaggctg agatggcgtt tcacggcctt ggactcagac tcttcctccc tcgattctga    1860
ttcctccgac aaattcgctg ccgggtattc aaattaagct ctttaaaccg atgttttgt    1920 tatgcccatg agagttgaac ccgtaaagtt acagactttg gagtttaatc gtatttaagt    1980
ttctaaattt gattattttt ggtgcagctt ttgtatcata gaaggacctg aaacagtaca    2040
ggactttgcc aaaatgcaat tacaagagat tcaagacaac attagaagcc gtcgaaacaa    2100
gatcttcttg cacatggaag aggtttactt tcttaaagtg gaaacccttta gtttctaaaa    2160 ctgtcttcct ccttcgttaa ctatctgtta atacaggtac ggaggctaag aatacaacaa    2220
cggattagaa acacagagct tggaatcata gacgaagagc aagaacacga actaaagtcg    2280
cagaatccga acttggtatg atcgtatgaa cacaaactta ataaaacttt tgctttgtct    2340
tattaatctt tcttagcttt cttcttcttt tttcttatta aaaactctct tacacttagg    2400
cttcttatat aggcaataga aatcttaact tatcctatta catattaatc taggaatctt    2460
taacttagct tatctttatc ctaaatctat ttgtataagt tattcctctt tccttttga    2520 ataacttatt actcaagtaa cttttgaagct tatccaacat tctccctctt aagcttcaaa    2580 ccatttcac ttaggttttg aacttcaatc atcgacctca tttccttgaa tttgatcttg    2640
gccaatgctt tagttaggat gtctgctttc tgctctgttc ccggtacatg ttccacatca    2700
atgagattgc gctcaacaca ttccctaatg aagtgaaacc tcttgtggat atgcttgctt    2760
cgtcggtgaa agactggatt cttttgcaaga gatatagctg acttgttatc gactagaatc    2820
agtgtcttct ccgtctcacc tcctgttact tcactcaaga gttcttgtaa ccagatagcc    2880
tgtttagcag cctccgttgc agccatgaac tcggcttcgc aggatgacaa cgccactgtg    2940
tcttgtttct gagagcacca agtgattggt gtgtttccta gacagaacag gtgacctgtt    3000
gtgctccttc catcgtccgg atcagtattg tgactactgt cgctgtaccc tacaagtttc    3060
tgtgtacttc cacgtttaaa ctctagacca tgcccgagag ttccttgtag atatcttaaa    3120
acttgcttta acgcattccc gtgagactct ctcggtgatt gcatatatct acttaggatc    3180
ccaactgagt atgccatgtc tggtctagtg tgcattaagt accttaagca cccaatctt    3240 cttcgatatt gagttgcatc aatctctggt tcatccagtg cctttgagaa ttgtagaccg    3300
aactccattg gaatacaatt tggattgcaa tcggccatac ctgattcttc catgatccgt    3360
tttgcatagg cttcttgttt gattgtgatc cctctagtgc tctgctttac ttcaatgcct    3420
agataatagg ttagcaaccc gagatcagac atttcaaact tgtgtgacat cgctgtcttg    3480
aactctttga tgatctttgt tgaatttcct gtaacaaaga gatcatccac atatattgcg    3540
ataatcagaa gcttatctcc ttcttctctt ctgtagaccg agctttcttt catgcacttc    3600
ttgaaccgca aactcttaag aacgcgatcg agtttagtat tccaagcgcg aggagcttgc    3660
cttagaccat atagtgcctt tgagagtttg aaaactttat gttcttctcc cttttttca    3720
```

```
aacccttcag gttgagttac atagacttct tcattcaatt ctccatgtaa gaatgccgtc    3780
ttgacgtcta ggtggtgaag ttcccatccc tttgcagaag ctaagctgat taagagtcga    3840
atggactcta tacgagctac tggagcaaac acttcttcaa aatcaattcc atgctcttgt    3900
acatatccct ttgctacaag tcttgctttg aatttgttga ttgatccatc tgcgttcctt    3960
ttgatcttga aaatccactt aagaccaatg actttaactc cgtgtggctt atctaccaac    4020
ttccatgtct ggtttctgtt gatagagtca atctcatctt cgcatgcttt tgtccatcga    4080
acatgtatct tagcttcttg gtatgttgat ggttcatcgt tgattgaaca caggagtagt    4140
tcgcattcta tctcggcgag tagaatgtaa tcttctaggt gtttgggaag ttttacttct    4200
ctagatgatc ttcttggttc gacgtgatct acctcggggg ttggctctgt tgtttcttct    4260
tgttgttcag tctcagttgc aatatttttct tcctgatgtg aacctatgac aaacggaccg    4320
ttaccctcgt ctatgcttga tccccacgtc atgtggaact tgccagattc ttcttggttt    4380
cctttatctg tttcattcca gttccagcat gctttctcat cgaacttcac gtctcgacta    4440
accacaatcc ttctcgtgct aggattatat aagcggtaag ctttcgaccc tggttctata    4500
ccaaggtgaa ccagtgtctg tgatctgtca tcgagtttct tcaaaagggc agcatcgagt    4560
ttggcatatg ccaaacagcc aaagactctg atgtgtccaa tgctcggctt tcttcctttg    4620
aaactctcat aaggagtttg attcttcaaa gctctagttg gaactcgatt gatcagatac    4680
gttgcatgtc gaacagcctc tccccacata taatttggaa cattcatcgc ttttaacata    4740
ctgcgcgtca tctccattaa cgttcggttt cttctttcga caacgccgtt tgctgtggc     4800 gtatatggcg cagttagatg tctcctaata ccattgttgt tgcagtaatc ttgaaagtct    4860
cttgaagtaa actctccgcc tctatctgtg cgaagtgtta ctattacttt attgacctcc    4920
ttctctacaa gagctttaaa ggtcttgaat ttctcaaaga cttcactttt ttctttgagt    4980
aaaatagacc acatgtatct tgtgttgtca tcaattatga caaatatgta ccggttctgt    5040
gccagtgttg aaggagagat tggaccgcag aggtcagcgt gcaacaactc taatacctgc    5100
gacgacctat gtggtgttgc agagggaaaa ctatttcgag tctgtttccc aacgagacac    5160
gactcacaaa gcttcttctc ttcgttgatc tcaggtagtc ctcgaaccat ctcgagtttt    5220
gccatgtctt ttatcgtctt gaagttgata tggccaaggc gtgcgtgcca tctccacggt    5280
tcttcattaa tctttgtgag aaggcagctt ggttttccaa ctttgagtga taccttgtag    5340
agacgattag gtgatcttaa gacttttaca agtaacctcc cgcttggatc tctcaaagtc    5400
agatagttat ctttcattct tacatcacag ccttgttcag ttgcttggcc taggctcaga    5460
atgttgcttc ttaactctgg tatataatat atattagtta gaagcttttg ctctcccgtc    5520
tttgcttcaa agataattga gccttttgcca ttgattttca cacatgatcc atcaccaaac    5580
ttaactcttc ccttgatact ttcattgagt tcggagaaga agctcttgtc tcctgtcata    5640
tgattactag caccgttgtc aagataccaa ttaccatcat cagttttgtt ttgctcaagt    5700
ttctttggca tcacgctttc ttcattcaaa aacacaactt catgcatgta taatgctgct    5760
tcagctactt ctgtctctgc tttgttgagt tgatgatcat cattcttctc gggacagaca    5820
gaggcaaagt gacccttctt gtggcagtga aagcactcga tttgagagta atccttcttc    5880
tctttatttc tctcacctcc gttgctacta ccacgccccc ttcctctgtt cccacgaccc    5940
ctattggaac ctcgtcctct gcctttggtt ccatgatcgg agtagaggag cttgccatta    6000
tcttcaagtt tctctcctcg cattctctct tctccacgca agcgttcctc aaatgctttg    6060
aggcgaccta ccacatcttc gtaccttgtg ttgtttaggt caagaacttg ttctagtgtt    6120
```

-continued

```
gctgagagct gaagaaattt acttggcaga catgatagaa acttctttac tagttttgct   6180
tcctctatcg tatggccgag tgatgcaact gttcctgcaa actctgataa ttttccggag   6240
aacgtatcta tcgaatcagt atctttcatt ctcagatgat cgaactcaat agactatcca   6300
ctcaatcatc agtgtgtgca ggcgtgcttc tattactcga tcagctccaa tattcattgc   6360
tttcaatgct tcccacatac ctttaggaga gtcttgctcc ccaacttgta ggattaagtt   6420
ctctggaatt ccttgaaaca agagaatcgt agctaggtca ttcttctttt ggtcctttga   6480
tcctggatca atggtttccc atacctcatg aaacctaaat agaaccttca tccttaaaga   6540
ccagacagca tagttcgttg ttgtgagcat tggtgttttg acagagggtg gtaacgcgct   6600
tagcttcata gctggttttg tctctgaatc actcatgatt agattaactc atgctctgat   6660
accaaataaa gtcgcagaat ccgaacttgg tatgatcgta tgaacacaaa cttaataaaa   6720
cttttgcttt gtcttattaa tctttcttag ctttcttctt cttttttctt attaaaaact   6780
ctcttacact taggcttctt atataggcaa tagaaatctt aacttatcct attacatatt   6840
aatctaggaa tctttaactt agcttatctt tatcctaaat ctatttgtat aagttattcc   6900
tctttccttt ttgaataact tattactcaa gtaactttga agcttatcca acacgaacta   6960
cctaacttcc cctccttcat cccattctta cctccattgg taagtattta aacactttct   7020
ttagaggagg attttgtgtg ttttgaattg atcaataaat acactttcat tttgctagac   7080
tgctgccaat ttgagagtct attacgcaac ttgcttctca ctcattgctg ggattatcct   7140
cttcggtggc ctactagctc ctactgtaag ccctttgctt caagattggc atatactccc   7200
tccctttga aaaaatccac gttttagaga atttttttt gtttcaaata gatatatctt   7260
cattttcaaa tgcattattt aatggtaaat tataaacttc aaaaaaagat aattgtgttt   7320
attgaaattt attggttaag ttgcgggaaa atcgttaata accaaaaaaa aaacaattca   7380
ttaataatca gtatttaata tgttttttga aaccagaggg tgtatgagta tttctttgct   7440
ttatgtaata aagtttttga tttgtaactt ctgcagctag agctgaagct aggtataggg   7500
ggcacatcat ataaagattt cattcaaagc cttcatctac ctatgcaatt gaggtttagt   7560
atctctcttt atatacattt gcaactttat agaaaggatg cttaactctt gtgtgttcac   7620
cagtcaagta gacccaatag tggcgtcatt ctctggagga gctgttggtg tgatctcagc   7680
tttgatggta gttgaagtta acaacgtgaa gcagcaagag cacaagagat gcaaatactg   7740
tctaggaact ggtaattatg tttcctcttc ttgttcataa agagatttaa gttgttggtt   7800
ttaataactt ttcttatgta acacacacag ggtatctagc atgtgcccgt tgctctagca   7860
caggttctct tattatatct gaaccagtct cagctattgc tggagggaac cattctgtat   7920
caacatccaa aaccgaaaga tgttcaaact gttctggtgc tggaaaggta taaaccatca   7980
aaaaccaaaa cctaaaagcc caaaaccaaa aatgtggatg ttgaattgtc tgtgtttgtt   8040
gttcaggtga tgtgtccgac atgtctgtgc acaggagtgg ctatggctag cgagcacgac   8100
cctcgtattg atcccttcct ttgattcctc tcccccccca caaaatctat ttgtcattgt   8160
aactaaaaat ggtatgtact aatgaataat gagaactgca tcctttcatc tgtatatgta   8220
cacacacaat gacacaaatg aacttattac ataatgttag atttttcttc gtcctgtaac   8280
actccgaaag ctcaacactc tccagaatta gagccagaaa cgaaacacac tgtttctagg   8340
ctatatgtgg cttagagttg agtacactac ttagtaggtc tgggcgttcg gacccgtcgg   8400
tttcggttcg gttgattcgg atttttggtg ttatgctcat aagtcccttt cgggttttat   8460
taatcttcga gtcgggtttg gttcggtttc cttccggaaa tgtttgaaat cgtccaaaaa   8520
```

```
tatgtttttt aaacctcaaa aaatgataaa tattttttca taatatagaa attattcaca    8580
aatctaatta aaattagtta aaatatttaa attaactaaa aagtattcaa aataacaaat    8640
aaaacaaact acaaaaatat tttgaatact ctaaaatatc taaatcactt caacgtatat    8700
aaaaacatta acacatttaa ctaatttcaa atatcttcgg atcctagttt ggatttcggt    8760
tcggttcgtt ttataaccaa accccaaaat actaagctta taagtctcgt tcggatattt    8820
ttgtataaca gtttggatcc ggtttcggtt tttccagttc gggtttaggt aggattggag    8880
taaaaacgcc caggcctact agttagtagc ttagtgagta aaattaggtt ctaagatgat    8940
aatcgcttct aagtaatact tttcactaat tctcagctta ctgatgttga cactgttact    9000
tcttcaggct ccaaatctag tttacttcca ttgaaacttc attaaaactc atatgaaaaa    9060
gtacagtaca atggtttggt tcggcaggac ataaccaaat tatacaatcg aaagagacac    9120
aagtctgtat ccaaacacag ttagcccaag gaaggaagaa ctggagatta ttatttgaag    9180
ggacacagtt agttagtccc tagtgcccat tctcgcagcg gttgtct                 9227

<210> SEQ ID NO 2
<211> LENGTH: 915
<212> TYPE: DNA
<213> ORGANISM: Brassica oleracea

<400> SEQUENCE: 2
atgtcttgtt tgggtaggat cttgtctgtt tcctacccac cggatccgta cggttcgcgt     60
ctttcagtgt caaagctgtc ttcaccaggg agaaaccgaa ggctgagatg gcgtttcacg    120
gccttggact cagactcttc ctccctcgat tctgattcct ccgacaaatt cgctgccggc    180
ttttgtatca tagaaggacc tgaaacagta caggactttg ccaaaatgca attcaagag     240 attcaagaca acattagaag ccgtcgaaac aagatcttct gcacatggaa agaggtacgg    300
aggctaagaa tacaacaacg gattagaaac acagagcttg gaatcataga cgaagagcaa    360
gaacacgaac tacctaactt cccctccttc atcccattct tacctccatt gactgctgcc    420
aatttgagag tctattacgc aacttgcttc tcactcattg ctgggattat cctcttcggt    480
ggcctactag ctcctactct agagctgaag ctaggtatag ggggcacatc atataaagat    540
ttcattcaaa gccttcatct acctatgcaa ttgagtcaag tagacccaat agtggcgtca    600
ttctctggag gagctgttgg tgtgatctca gctttgatgg tagttgaaat taacaacgtg    660
aagcagcaag agcacaagag atgcaaatac tgtctaggaa ctgggtatct agcatgtgcc    720
cgttgctcta gcacaggttc tcttattata tctgaaccag tctcagctat tgctggaggg    780
aaccattctg tatcaacatc caaaaccgaa agatgttcaa actgttctgg tgctggaaag    840
gtgatgtgtc cgacatgtct gtgcacagga atggctatgg ctagcgagca cgaccctcgt    900
attgatccct tcctt                                                    915

<210> SEQ ID NO 3
<211> LENGTH: 1162
<212> TYPE: DNA
<213> ORGANISM: Brassica oleracea

<400> SEQUENCE: 3
ccaaaactaa accacactga cagacacaca taaaagaaca ggcaaactaa ttgatccgct     60
gctgaagatc tcgaaaccat gtcttgtttg ggtaggatct tgtctgtttc ctacccaccg    120
gatccgtacg gttcgcgtct ttcagtgtca aagctgtctt caccagggag aaaccgaagg    180
ctgagatggc gtttcacggc cttggactca gactcttcct ccctcgattc tgattcctcc    240
```

| | |
|---|---|
| gacaaattcg ctgccggctt ttgtatcata gaaggacctg aaacagtaca ggactttgcc | 300 |
| aaaatgcaat tacaagagat tcaagacaac attagaagcc gtcgaaacaa gatcttcttg | 360 |
| cacatggaag aggtacggag gctaagaata caacaacgga ttagaaacac agagcttgga | 420 |
| atcatagacg aagagcaaga acacgaacta cctaacttcc cctccttcat cccattctta | 480 |
| cctccattga ctgctgccaa tttgagagtc tattacgcaa cttgcttctc actcattgct | 540 |
| gggattatcc tcttcggtgg cctactagct cctactctag agctgaagct aggtataggg | 600 |
| ggcacatcat ataaagattt cattcaaagc cttcatctac ctatgcaatt gagtcaagta | 660 |
| gacccaaatag tggcgtcatt ctctggagga gctgttggtg tgatctcagc tttgatggta | 720 |
| gttgaagtta acaacgtgaa gcagcaagag cacaagagat gcaaatactg tctaggaact | 780 |
| gggtatctag catgtgcccg ttgctctagc acaggttctc ttattatatc tgaaccagtc | 840 |
| tcagctattg ctggagggaa ccattctgta tcaacatcca aaaccgaaag atgttcaaac | 900 |
| tgttctggtg ctggaaaggt gatgtgtccg acatgtctgt gcacaggaat ggctatggct | 960 |
| agcgagcacg accctcgtat tgatcccttc ctttgattcc actccccacc ccccaccaaa | 1020 |
| atctatttgt cattgtaact aaaaatggta tgtaaatgag aactgcatcc tttcatctgt | 1080 |
| atatgtacac acacaatgac acaaatggaa cttattacat aatgttagat ttttacaaaa | 1140 |
| aaaaaaaaaa aaaaaaaaa aa | 1162 |

<210> SEQ ID NO 4
<211> LENGTH: 1078
<212> TYPE: DNA
<213> ORGANISM: Brassica oleracea

<400> SEQUENCE: 4

| | |
|---|---|
| ccaaaactaa accacactga cagacacaca taaaagaaca ggcaaactaa ttgatccgct | 60 |
| gctgaagatc tcgaaaccat gtcttgtttg ggtaggatct tgtctgtttc ctacccaccg | 120 |
| gatccttccg gttcgcgtct ttcagtgtca agctgtcttc caccagggag aaaccgaagg | 180 |
| ctgagatggc gtttcacggc cttggactca gactcttcct ccctcgattc tgattcctcc | 240 |
| gacaaattcg ctgccggctt ttgtatcata gaaggacctg aaacagtaca ggactttgcc | 300 |
| aaaatgcaat tacaagagat tcaagacaac attagaagcc gtcgaaacaa gatcttcttg | 360 |
| cacatggaag aggtacggag gctaagaata caacaacgga ttagaaacac agagcttgga | 420 |
| atcatagacg aagagcaaga acacgaacta agtcgcaga atccgaactt gactgctgcc | 480 |
| aatttgagag tctattacgc aacttgcttc tcactcattg ctgggattat cctcttcggt | 540 |
| ggcctactag ctcctactct agagctgaag ctaggtatag ggggcacatc atataaagat | 600 |
| ttcattcaaa gccttcatct acctatgcaa ttgagtcaag tagacccaat agtggcgtca | 660 |
| ttctctggag gagctgttgg tgtgatctca gctttgatgg tagttgaagt taacaacgtg | 720 |
| aagcagcaag agcacaagag atgcaaatac tgtctaggaa ctgggtatct agcatgtgcc | 780 |
| cgttgctcta gcacaggttc tcttattata tctgaaccag tctcagctat gctggaggg | 840 |
| aaccattctg tatcaacatc caaaaccgaa agatgttcaa actgttctgg tgctggaaag | 900 |
| gtgatgtgtc cgacatgtct gtgcacagga gtggctatgg ctagcgagca cgaccctcgt | 960 |
| attgatccct cctttgatt cctctccccc cccacaaaat ctatttgtca ttgtaactaa | 1020 |
| aaatggtatg tactaatgaa taatgagaac tgcatccttt catctgtata tgtacaca | 1078 |

<210> SEQ ID NO 5
<211> LENGTH: 1135
<212> TYPE: DNA

<213> ORGANISM: Brassica oleracea

<400> SEQUENCE: 5

```
ccaaaactaa accacactga cagacacaca taaaagaaca ggcaaactaa ttgatccgct      60
gctgaagatc tcgaaaccat gtcttgtttg ggtaggatct tgtctgtttc ctacccaccg     120
gatccttccg gttcgcgtct ttcagtgtca aagctgtctt caccagggag aaaccgaagg     180
ctgagatggc gtttcacggc cttggactca gactcttcct ccctcgattc tgattcctcc     240
gacaaattcg ctgccggctt tgtatcata gaaggacctg aaacagtaca ggactttgcc     300
aaaatgcaat tacaagagat tcaagacaac attagaagcc gtcgaaacaa gatcttcttg     360
cacatggaag aggtacggag ctaagaata caacaacgga ttagaaacac agagcttgga     420
atcatagacg aagagcaaga acacgaacta agtcgcaga atccgaactt gcttatccaa      480
cacgaactac ctaacttccc ctccttcatc ccattcttac ctccattgac tgctgccaat     540
ttgagagtct attcgcaac ttgcttctca ctcattgctg ggattatcct cttcggtggc      600
ctactagctc ctactctaga gctgaagcta ggtatagggg gcacatcata taaagatttc     660
attcaaagcc ttcatctacc tatgcaattg agtcaagtag acccaatagt ggcgtcattc     720
tctggaggag ctgttggtgt gatctcagct ttgatggtag ttgaagttaa caacgtgaag     780
cagcaagagc acaagagatg caaatactgt ctaggaactg ggtatctagc atgtgcccgt     840
tgctctagca caggttctct tattatatct gaaccagtct cagctattgc tggagggaac     900
cattctgtat caacatccaa aaccgaaaga tgttcaaact gttctggtgc tggaaaggtg     960
atgtgtccga catgtctgtg cacaggagtg gctatggcta gcgagcacga ccctcgtatt    1020
gatcccttcc tttgattcct ctcccccccc acaaaatcta tttgtcattg taactaaaaa    1080
tggtatgtac taatgaataa tgagaactgc atcctttcat ctgtatatgt acaca         1135
```

<210> SEQ ID NO 6
<211> LENGTH: 992
<212> TYPE: DNA
<213> ORGANISM: Brassica oleracea

<400> SEQUENCE: 6

```
ccaaaactaa accacactga cagacacaca taaaagaaca ggcaaactaa ttgatccgct      60
gctgaagatc tcgaaaccat gtcttgtttg ggtaggatct tgtctgtttc ctacccaccg     120
gatccttccg gttcgcgtct ttcagtgtca aagctgtctt caccagggag aaaccgaagg     180
ctgagatggc gtttcacggc cttggactca gactcttcct ccctcgattc tgattcctcc     240
gacaaattcg ctgccggctt tgtatcata gaaggacctg aaacagtaca ggactttgcc     300
aaaatgcaat tacaagagat tcaagacaac attagaagcc gtcgaaacaa gatcttcttg     360
cacatggaag aggtacggag ctaagaata caacaacgga ttagaaacac agagcttgga     420
atcatagacg aagagcaaga acacgaacta agtcgcaga atccgaactt gctagagctg     480
aagctaggta taggggcac atcatataaa gatttcattc aaagccttca tctacctatg     540
caattgagtc aagtagaccc aatagtggcg tcattctctg gaggagctgt tggtgtgatc    600
tcagctttga tggtagttga agttaacaac gtgaagcagc aagagcacaa gagatgcaaa    660
tactgtctag gaactgggta tctagcatgt gcccgttgct ctagcacagg ttctcttatt    720
atatctgaac cagtctcagc tattgctgga gggaaccatt ctgtatcaac atccaaaacc    780
gaaagatgtt caaactgttc tggtgctgga aaggtgatgt gtccgacatg tctgtgcaca    840
ggagtggcta tggctagcga gcacgaccct cgtattgatc ccttcctttg attcctctcc    900
```

```
cccccccacaa aatctatttg tcattgtaac taaaaatggt atgtactaat gaataatgag    960
aactgcatcc tttcatctgt atatgtacac aa                                  992
```

<210> SEQ ID NO 7
<211> LENGTH: 305
<212> TYPE: PRT
<213> ORGANISM: Brassica oleracea

<400> SEQUENCE: 7

```
Met Ser Cys Leu Gly Arg Ile Leu Ser Val Ser Tyr Pro Pro Asp Pro
1               5                  10                  15

Tyr Gly Ser Arg Leu Ser Val Ser Lys Leu Ser Ser Pro Gly Arg Asn
            20                  25                  30

Arg Arg Leu Arg Trp Arg Phe Thr Ala Leu Asp Ser Asp Ser Ser Ser
        35                  40                  45

Leu Asp Ser Asp Ser Ser Asp Lys Phe Ala Ala Gly Phe Cys Ile Ile
    50                  55                  60

Glu Gly Pro Glu Thr Val Gln Asp Phe Ala Lys Met Gln Leu Gln Glu
65                  70                  75                  80

Ile Gln Asp Asn Ile Arg Ser Arg Arg Asn Lys Ile Phe Leu His Met
                85                  90                  95

Glu Glu Val Arg Arg Leu Arg Ile Gln Gln Arg Ile Arg Asn Thr Glu
            100                 105                 110

Leu Gly Ile Ile Asp Glu Glu Gln Glu His Glu Leu Pro Asn Phe Pro
        115                 120                 125

Ser Phe Ile Pro Phe Leu Pro Pro Leu Thr Ala Ala Asn Leu Arg Val
    130                 135                 140

Tyr Tyr Ala Thr Cys Phe Ser Leu Ile Ala Gly Ile Ile Leu Phe Gly
145                 150                 155                 160

Gly Leu Leu Ala Pro Thr Leu Glu Leu Lys Leu Gly Ile Gly Gly Thr
                165                 170                 175

Ser Tyr Lys Asp Phe Ile Gln Ser Leu His Leu Pro Met Gln Leu Ser
            180                 185                 190

Gln Val Asp Pro Ile Val Ala Ser Phe Ser Gly Gly Ala Val Gly Val
        195                 200                 205

Ile Ser Ala Leu Met Val Val Glu Val Asn Asn Val Lys Gln Gln Glu
    210                 215                 220

His Lys Arg Cys Lys Tyr Cys Leu Gly Thr Gly Tyr Leu Ala Cys Ala
225                 230                 235                 240

Arg Cys Ser Ser Thr Gly Ser Leu Ile Ile Ser Glu Pro Val Ser Ala
                245                 250                 255

Ile Ala Gly Gly Asn His Ser Val Ser Thr Ser Lys Thr Glu Arg Cys
            260                 265                 270

Ser Asn Cys Ser Gly Ala Gly Lys Val Met Cys Pro Thr Cys Leu Cys
        275                 280                 285

Thr Gly Met Ala Met Ala Ser Glu His Asp Pro Arg Ile Asp Pro Phe
    290                 295                 300

Leu
305
```

<210> SEQ ID NO 8
<211> LENGTH: 299
<212> TYPE: PRT
<213> ORGANISM: Brassica oleracea

<400> SEQUENCE: 8

```
Met Ser Cys Leu Gly Arg Ile Leu Ser Val Ser Tyr Pro Pro Asp Pro
1               5                   10                  15

Ser Gly Ser Arg Leu Ser Val Ser Lys Leu Ser Ser Pro Gly Arg Asn
            20                  25                  30

Arg Arg Leu Arg Trp Arg Phe Thr Ala Leu Asp Ser Asp Ser Ser
            35                  40                  45

Leu Asp Ser Asp Ser Ser Asp Lys Phe Ala Ala Gly Phe Cys Ile Ile
        50                  55                  60

Glu Gly Pro Glu Thr Val Gln Asp Phe Ala Lys Met Gln Leu Gln Glu
65                  70                  75                  80

Ile Gln Asp Asn Ile Arg Ser Arg Asn Lys Ile Phe Leu His Met
                85                  90                  95

Glu Glu Val Arg Arg Leu Arg Ile Gln Gln Arg Ile Arg Asn Thr Glu
                100                 105                 110

Leu Gly Ile Ile Asp Glu Glu Gln Glu His Glu Leu Lys Ser Gln Asn
            115                 120                 125

Pro Asn Leu Thr Ala Ala Asn Leu Arg Val Tyr Tyr Ala Thr Cys Phe
        130                 135                 140

Ser Leu Ile Ala Gly Ile Ile Leu Phe Gly Gly Leu Leu Ala Pro Thr
145                 150                 155                 160

Leu Glu Leu Lys Leu Gly Ile Gly Gly Thr Ser Tyr Lys Asp Phe Ile
                165                 170                 175

Gln Ser Leu His Leu Pro Met Gln Leu Ser Gln Val Asp Pro Ile Val
            180                 185                 190

Ala Ser Phe Ser Gly Gly Ala Val Gly Val Ile Ser Ala Leu Met Val
            195                 200                 205

Val Glu Val Asn Asn Val Lys Gln Gln Glu His Lys Arg Cys Lys Tyr
210                 215                 220

Cys Leu Gly Thr Gly Tyr Leu Ala Cys Ala Arg Cys Ser Ser Thr Gly
225                 230                 235                 240

Ser Leu Ile Ile Ser Glu Pro Val Ser Ala Ile Ala Gly Gly Asn His
                245                 250                 255

Ser Val Ser Thr Ser Lys Thr Glu Arg Cys Ser Asn Cys Ser Gly Ala
            260                 265                 270

Gly Lys Val Met Cys Pro Thr Cys Leu Cys Thr Gly Val Ala Met Ala
            275                 280                 285

Ser Glu His Asp Pro Arg Ile Asp Pro Phe Leu
        290                 295

<210> SEQ ID NO 9
<211> LENGTH: 318
<212> TYPE: PRT
<213> ORGANISM: Brassica oleracea

<400> SEQUENCE: 9

Met Ser Cys Leu Gly Arg Ile Leu Ser Val Ser Tyr Pro Pro Asp Pro
1               5                   10                  15

Ser Gly Ser Arg Leu Ser Val Ser Lys Leu Ser Ser Pro Gly Arg Asn
            20                  25                  30

Arg Arg Leu Arg Trp Arg Phe Thr Ala Leu Asp Ser Asp Ser Ser
            35                  40                  45

Leu Asp Ser Asp Ser Ser Asp Lys Phe Ala Ala Gly Phe Cys Ile Ile
        50                  55                  60

Glu Gly Pro Glu Thr Val Gln Asp Phe Ala Lys Met Gln Leu Gln Glu
65                  70                  75                  80
```

```
Ile Gln Asp Asn Ile Arg Ser Arg Arg Asn Lys Ile Phe Leu His Met
                85                  90                  95

Glu Glu Val Arg Arg Leu Arg Ile Gln Gln Arg Ile Arg Asn Thr Glu
            100                 105                 110

Leu Gly Ile Ile Asp Glu Glu Gln Glu His Glu Leu Lys Ser Gln Asn
        115                 120                 125

Pro Asn Leu Leu Ile Gln His Glu Leu Pro Asn Phe Pro Ser Phe Ile
    130                 135                 140

Pro Phe Leu Pro Pro Leu Thr Ala Ala Asn Leu Arg Val Tyr Tyr Ala
145                 150                 155                 160

Thr Cys Phe Ser Leu Ile Ala Gly Ile Ile Leu Phe Gly Gly Leu Leu
                165                 170                 175

Ala Pro Thr Leu Glu Leu Lys Leu Gly Ile Gly Gly Thr Ser Tyr Lys
            180                 185                 190

Asp Phe Ile Gln Ser Leu His Leu Pro Met Gln Leu Ser Gln Val Asp
        195                 200                 205

Pro Ile Val Ala Ser Phe Ser Gly Gly Ala Val Gly Val Ile Ser Ala
    210                 215                 220

Leu Met Val Val Glu Val Asn Asn Val Lys Gln Gln Glu His Lys Arg
225                 230                 235                 240

Cys Lys Tyr Cys Leu Gly Thr Gly Tyr Leu Ala Cys Ala Arg Cys Ser
                245                 250                 255

Ser Thr Gly Ser Leu Ile Ile Ser Glu Pro Val Ser Ala Ile Ala Gly
            260                 265                 270

Gly Asn His Ser Val Ser Thr Ser Lys Thr Arg Cys Ser Asn Cys
        275                 280                 285

Ser Gly Ala Gly Lys Val Met Cys Pro Thr Cys Leu Cys Thr Gly Val
    290                 295                 300

Ala Met Ala Ser Glu His Asp Pro Arg Ile Asp Pro Phe Leu
305                 310                 315

<210> SEQ ID NO 10
<211> LENGTH: 270
<212> TYPE: PRT
<213> ORGANISM: Brassica oleracea

<400> SEQUENCE: 10

Met Ser Cys Leu Gly Arg Ile Leu Ser Val Ser Tyr Pro Pro Asp Pro
1               5                   10                  15

Ser Gly Ser Arg Leu Ser Val Ser Lys Leu Ser Ser Pro Gly Arg Asn
            20                  25                  30

Arg Arg Leu Arg Trp Arg Phe Thr Ala Leu Asp Ser Asp Ser Ser
        35                  40                  45

Leu Asp Ser Asp Ser Ser Asp Lys Phe Ala Ala Gly Phe Cys Ile Ile
    50                  55                  60

Glu Gly Pro Glu Thr Val Gln Asp Phe Ala Lys Met Gln Leu Gln Glu
65                  70                  75                  80

Ile Gln Asp Asn Ile Arg Ser Arg Arg Asn Lys Ile Phe Leu His Met
                85                  90                  95

Glu Glu Val Arg Arg Leu Arg Ile Gln Gln Arg Ile Arg Asn Thr Glu
            100                 105                 110

Leu Gly Ile Ile Asp Glu Glu Gln Glu His Glu Leu Lys Ser Gln Asn
        115                 120                 125

Pro Asn Leu Leu Glu Leu Lys Leu Gly Ile Gly Gly Thr Ser Tyr Lys
    130                 135                 140
```

```
Asp Phe Ile Gln Ser Leu His Leu Pro Met Gln Leu Ser Gln Val Asp
145                 150                 155                 160

Pro Ile Val Ala Ser Phe Ser Gly Gly Ala Val Gly Val Ile Ser Ala
                165                 170                 175

Leu Met Val Val Glu Val Asn Asn Val Lys Gln Gln Glu His Lys Arg
            180                 185                 190

Cys Lys Tyr Cys Leu Gly Thr Gly Tyr Leu Ala Cys Ala Arg Cys Ser
        195                 200                 205

Ser Thr Gly Ser Leu Ile Ile Ser Glu Pro Val Ser Ala Ile Ala Gly
    210                 215                 220

Gly Asn His Ser Val Ser Thr Ser Lys Thr Glu Arg Cys Ser Asn Cys
225                 230                 235                 240

Ser Gly Ala Gly Lys Val Met Cys Pro Thr Cys Leu Cys Thr Gly Val
                245                 250                 255

Ala Met Ala Ser Glu His Asp Pro Arg Ile Asp Pro Phe Leu
            260                 265                 270

<210> SEQ ID NO 11
<211> LENGTH: 13
<212> TYPE: PRT
<213> ORGANISM: Brassica oleracea

<400> SEQUENCE: 11

Lys Ser Gln Asn Pro Asn Leu Leu Ile Gln His Glu Leu
1               5                   10

<210> SEQ ID NO 12
<211> LENGTH: 7
<212> TYPE: PRT
<213> ORGANISM: Brassica oleracea

<400> SEQUENCE: 12

Lys Ser Gln Asn Pro Asn Leu
1               5

<210> SEQ ID NO 13
<211> LENGTH: 307
<212> TYPE: PRT
<213> ORGANISM: Arabidopsis thaliana

<400> SEQUENCE: 13

Met Ser Ser Leu Gly Arg Ile Leu Ser Val Ser Tyr Pro Pro Asp Pro
1               5                   10                  15

Tyr Thr Trp Arg Phe Ser Gln Tyr Lys Leu Ser Ser Ser Leu Gly Arg
            20                  25                  30

Asn Arg Arg Leu Arg Trp Arg Phe Thr Ala Leu Asp Pro Glu Ser Ser
        35                  40                  45

Ser Leu Asp Ser Glu Ser Ser Ala Asp Lys Phe Ala Ser Gly Phe Cys
    50                  55                  60

Ile Ile Glu Gly Pro Glu Thr Val Gln Asp Phe Ala Lys Met Gln Leu
65                  70                  75                  80

Gln Glu Ile Gln Asp Asn Ile Arg Ser Arg Asn Lys Ile Phe Leu
                85                  90                  95

His Met Glu Glu Val Arg Arg Leu Arg Ile Gln Gln Arg Ile Lys Asn
            100                 105                 110

Thr Glu Leu Gly Ile Ile Asn Glu Glu Gln Glu His Glu Leu Pro Asn
        115                 120                 125

Phe Pro Ser Phe Ile Pro Phe Leu Pro Pro Leu Thr Ala Ala Asn Leu
    130                 135                 140
```

```
Lys Val Tyr Tyr Ala Thr Cys Phe Ser Leu Ile Ala Gly Ile Ile Leu
145                 150                 155                 160

Phe Gly Gly Leu Leu Ala Pro Thr Leu Glu Leu Lys Leu Gly Ile Gly
            165                 170                 175

Gly Thr Ser Tyr Ala Asp Phe Ile Gln Ser Leu His Leu Pro Met Gln
        180                 185                 190

Leu Ser Gln Val Asp Pro Ile Val Ala Ser Phe Ser Gly Ala Val
        195                 200                 205

Gly Val Ile Ser Ala Leu Met Val Val Glu Val Asn Asn Val Lys Gln
    210                 215                 220

Gln Glu His Lys Arg Cys Lys Tyr Cys Leu Gly Thr Gly Tyr Leu Ala
225                 230                 235                 240

Cys Ala Arg Cys Ser Ser Thr Gly Ala Leu Val Leu Thr Glu Pro Val
                245                 250                 255

Ser Ala Ile Ala Gly Gly Asn His Ser Leu Ser Pro Pro Lys Thr Glu
                260                 265                 270

Arg Cys Ser Asn Cys Ser Gly Ala Gly Lys Val Met Cys Pro Thr Cys
                275                 280                 285

Leu Cys Thr Gly Met Ala Met Ala Ser Glu His Asp Pro Arg Ile Asp
    290                 295                 300

Pro Phe Asp
305

<210> SEQ ID NO 14
<211> LENGTH: 324
<212> TYPE: PRT
<213> ORGANISM: Hordeum vulgare

<400> SEQUENCE: 14

Met Leu Cys Ser Gly Arg Met Leu Ala Cys Ser Gly Leu Ser Pro Gly
1               5                   10                  15

Arg Leu Arg Pro Pro Arg Ala Tyr Ala Asp Arg Leu Arg Pro Pro Leu
            20                  25                  30

Pro Ala Arg Arg Trp Arg Val Ala Ala Ser Ala Ala Pro Gly Gly
        35                  40                  45

Ser Pro Asp Leu Pro Ser Ser Ser Ser Thr Pro Pro Phe Gly Ala
50                  55                  60

Gly Asp Asp Gln Ala Ala Ala Ala Ala Ser Ser Ser Gly Phe
65                  70                  75                  80

Cys Ile Ile Glu Gly Pro Glu Thr Val Gln Asp Phe Asp Lys Leu Asp
                85                  90                  95

Leu Gln Glu Ile Leu Asp Asn Ile Arg Ser Arg Arg Asn Lys Ile Phe
            100                 105                 110

Leu His Met Glu Glu Ile Arg Arg Leu Arg Ile Gln Gln Arg Ile Lys
        115                 120                 125

Asn Ala Glu Leu Gly Ile Ser Ile Glu Glu Pro Glu Gly Glu Leu Pro
    130                 135                 140

Asp Phe Pro Ser Phe Ile Pro Phe Leu Pro Leu Ser Ala Ala Asn
145                 150                 155                 160

Leu Lys Val Tyr Tyr Ala Thr Cys Phe Ser Leu Ile Ala Ala Ile Met
                165                 170                 175

Val Phe Gly Gly Phe Leu Ala Pro Ile Leu Glu Leu Lys Leu Gly Ile
            180                 185                 190

Gly Gly Thr Ser Tyr Ala Asp Phe Ile Arg Asn Val His Leu Pro Met
        195                 200                 205
```

```
Gln Leu Ser Gln Val Asp Pro Ile Val Ala Ser Phe Ser Gly Gly Ala
    210                 215                 220
Val Gly Val Ile Ser Ala Leu Met Val Val Glu Ile Asn Asn Val Lys
225                 230                 235                 240
Gln Gln Glu His Lys Arg Cys Lys Tyr Cys Leu Gly Thr Gly Tyr Leu
                245                 250                 255
Ala Cys Ala Arg Cys Ser Ser Thr Gly Ala Val Val Leu Thr Glu Pro
                260                 265                 270
Val Ser Thr Phe Ser Asp Gly Asp Gln Pro Leu Ser Ala Pro Lys Thr
                275                 280                 285
Glu Arg Cys Pro Asn Cys Ser Gly Ala Gly Lys Val Met Cys Pro Thr
                290                 295                 300
Cys Leu Cys Thr Gly Met Ala Met Ala Ser Glu His Asp Pro Arg Ile
305                 310                 315                 320
Asp Pro Phe Asp

<210> SEQ ID NO 15
<211> LENGTH: 326
<212> TYPE: PRT
<213> ORGANISM: Triticum aestivum

<400> SEQUENCE: 15

Met Leu Cys Ser Gly Arg Met Leu Ala Cys Ser Gly Leu Ser Pro Gly
1               5                   10                  15
Arg Leu Arg Pro Pro Arg Ala Tyr Ala Asp Arg Leu Arg Pro Pro Leu
                20                  25                  30
Pro Ala Arg Arg Trp Arg Val Ala Ala Ser Ala Ala Pro Gly Gly
                35                  40                  45
Ser Pro Asp Leu Pro Ser Ser Ser Thr Pro Pro Phe Gly Ala
    50                  55                  60
Gly Asp Asp Gln Ala Ala Ala Ala Ala Ala Ser Ser Ser Ser
65                  70                  75                  80
Gly Phe Cys Ile Ile Glu Gly Pro Glu Thr Val Gln Asp Phe Asp Lys
                85                  90                  95
Leu Asp Leu Gln Glu Ile Leu Asp Asn Ile Arg Ser Arg Arg Asn Lys
                100                 105                 110
Ile Phe Leu His Met Glu Glu Ile Arg Arg Leu Arg Ile Gln Gln Arg
                115                 120                 125
Ile Lys Asn Ala Glu Leu Gly Ile Ser Asn Glu Glu Pro Glu Gly Glu
                130                 135                 140
Leu Pro Asp Phe Pro Ser Phe Ile Pro Phe Leu Pro Pro Leu Ser Ala
145                 150                 155                 160
Ala Asn Leu Lys Val Tyr Tyr Ala Thr Cys Phe Ser Leu Ile Ala Ala
                165                 170                 175
Ile Met Val Phe Gly Gly Phe Leu Ala Pro Ile Leu Glu Leu Lys Leu
                180                 185                 190
Gly Ile Gly Gly Thr Ser Tyr Ala Asp Phe Ile Arg Asn Val His Leu
                195                 200                 205
Pro Met Gln Leu Ser Gln Val Asp Pro Ile Val Ala Ser Phe Ser Gly
    210                 215                 220
Gly Ala Val Gly Val Ile Ser Ala Leu Met Val Val Glu Ile Asn Asn
225                 230                 235                 240
Val Lys Gln Gln Glu His Lys Arg Cys Lys Tyr Cys Leu Gly Thr Gly
                245                 250                 255
```

-continued

```
Tyr Leu Ala Cys Ala Arg Cys Ser Ser Thr Gly Ala Val Val Leu Thr
            260                 265                 270

Glu Pro Val Ser Thr Phe Ser Asp Gly Asp Gln Pro Leu Ser Ala Pro
        275                 280                 285

Lys Thr Glu Arg Cys Pro Asn Cys Ser Gly Ala Gly Lys Val Met Cys
    290                 295                 300

Pro Thr Cys Leu Cys Thr Gly Met Ala Met Ser Glu His Asp Pro
305                 310                 315                 320

Arg Ile Asp Pro Phe Asp
                325

<210> SEQ ID NO 16
<211> LENGTH: 313
<212> TYPE: PRT
<213> ORGANISM: Gossypium arboreum

<400> SEQUENCE: 16

Met Val Cys Leu Ser Arg Val Leu Thr Ile Ser Cys Thr Val Lys Pro
1               5                   10                  15

Ser Pro Pro Tyr Lys Pro Ser Leu Ser Ser Arg Phe Val His Thr
            20                  25                  30

Lys Cys Glu Leu Lys Ser Arg Trp Arg Ser Met Ala Thr Glu Pro Asp
        35                  40                  45

Ser Ser Ser Ala Gln Ser Val Glu Ser Asp Ser Ala Asp Lys
    50                  55                  60

Thr Ala Ala Gly Phe Cys Ile Ile Glu Gly Pro Glu Thr Val Gln Asp
65                  70                  75                  80

Phe Ala Lys Met Glu Leu Gln Glu Ile Glu Asp Asn Ile Arg Ser Arg
                85                  90                  95

Arg Asn Lys Ile Phe Leu Gln Met Glu Glu Val Arg Arg Leu Arg Ile
            100                 105                 110

Gln Gln Arg Ile Lys Ser Ala Glu Leu Gly Ile Phe Lys Glu Glu Gln
        115                 120                 125

Glu Ser Glu Leu Pro Asn Phe Pro Ser Phe Ile Pro Phe Leu Pro Pro
    130                 135                 140

Leu Thr Ser Ala Asn Leu Lys Val Tyr Tyr Val Thr Cys Tyr Ser Leu
145                 150                 155                 160

Ile Ala Gly Ile Ile Phe Gly Gly Leu Leu Ala Pro Thr Leu Glu
                165                 170                 175

Leu Lys Leu Gly Leu Gly Gly Thr Ser Tyr Ala Asp Phe Ile Arg Ser
            180                 185                 190

Val His Leu Pro Met Gln Leu Ser Gln Val Asp Pro Ile Val Ala Ser
        195                 200                 205

Phe Ser Gly Gly Ala Val Gly Val Ile Ser Ala Leu Met Val Val Glu
    210                 215                 220

Ile Asn Asn Val Lys Gln Gln Glu His Lys Arg Cys Lys Tyr Cys Leu
225                 230                 235                 240

Gly Thr Gly Tyr Leu Ala Cys Ala Arg Cys Ser Ser Thr Gly Ser Leu
                245                 250                 255

Val Leu Thr Glu Pro Val Ser Thr Leu Asn Gly Gly Asp Arg Pro Leu
            260                 265                 270

Ser Thr Pro Arg Thr Glu Arg Cys Ser Asn Cys Leu Gly Ser Gly Lys
        275                 280                 285

Val Met Cys Pro Thr Cys Leu Cys Thr Gly Met Ala Met Ala Ser Glu
    290                 295                 300
```

```
His Asp Pro Arg Ile Asp Pro Phe Asp
305                 310
```

<210> SEQ ID NO 17
<211> LENGTH: 312
<212> TYPE: PRT
<213> ORGANISM: Vitis vinifera

<400> SEQUENCE: 17

```
Met Val Cys Ala Gly Arg Ile Leu Tyr Leu Ser Cys Ser Thr Thr Pro
1               5                   10                  15

Phe Ser Pro Ser Thr Ser Ala Phe Pro Thr Ser Thr Tyr Phe His Ala
            20                  25                  30

Asn Arg Arg Asn Gly Ile Arg Leu Arg Ser Met Ala Ser Asp Ala Asp
        35                  40                  45

Ala Ser Ser Tyr Ala Thr Ser Leu Asp Ser Glu Ser Ser Asp Arg Asn
    50                  55                  60

Ala Ala Gly Phe Cys Ile Ile Glu Gly Pro Glu Thr Val Glu Asp Phe
65                  70                  75                  80

Ala Lys Met Glu Leu Gln Glu Ile Arg Asp Asn Ile Arg Ser Arg Arg
                85                  90                  95

Asn Lys Ile Phe Leu His Met Glu Glu Val Arg Arg Leu Arg Ile Gln
            100                 105                 110

Gln Arg Ile Lys Ser Ala Glu Leu Gly Ile Ile Thr Glu Ala Gln Glu
        115                 120                 125

Asn Glu Leu Pro Asn Phe Pro Ser Phe Ile Pro Phe Leu Pro Pro Leu
    130                 135                 140

Thr Ser Ser Asn Leu Lys Gln Tyr Tyr Ala Thr Cys Ile Ser Leu Ile
145                 150                 155                 160

Ala Gly Phe Met Leu Phe Gly Gly Leu Leu Ala Pro Ser Leu Glu Leu
                165                 170                 175

Lys Leu Gly Leu Gly Gly Thr Ser Tyr Ala Asp Phe Ile Gly Ser Met
            180                 185                 190

His Leu Pro Met Gln Leu Ser Gln Val Asp Pro Ile Val Ala Ser Phe
        195                 200                 205

Ser Gly Gly Ala Val Gly Val Ile Ser Ala Leu Met Val Val Glu Ile
    210                 215                 220

Asn Asn Val Lys Gln Gln Glu His Lys Arg Cys Lys Tyr Cys Leu Gly
225                 230                 235                 240

Thr Gly Tyr Leu Ala Cys Ala Arg Cys Ser Asn Thr Gly Ser Leu Val
                245                 250                 255

Leu Ile Glu Pro Val Ser Thr Ile Tyr Gly Ala Asp Lys Pro Leu Ser
            260                 265                 270

Pro Pro Lys Thr Glu Arg Cys Ser Asn Cys Ser Gly Ser Gly Lys Val
        275                 280                 285

Met Cys Pro Thr Cys Leu Cys Thr Gly Met Ala Met Ala Ser Glu His
    290                 295                 300

Asp Pro Arg Ile Asp Pro Phe Asp
305                 310
```

<210> SEQ ID NO 18
<211> LENGTH: 321
<212> TYPE: PRT
<213> ORGANISM: Zea mays

<400> SEQUENCE: 18

```
Met Leu Cys Ser Gly Arg Met Leu Ala Cys Asn Gly Val Leu Pro Gly
```

```
                1               5                   10                  15
        Arg Leu Arg Leu Pro Arg Ala Asp Ala Tyr His Leu Arg Pro Pro Ala
                        20                  25                  30

Leu Ala Arg Arg Trp Arg Val Val Ala Ser Ala Ala Ser Gly Gly
                        35                  40                  45

Ser Pro Asp Leu Pro Ser Ser Ser Ser Pro Pro Asn Pro Pro Phe
            50                  55                  60

Gly Ala Gly Asp Asp Gln Thr Ala Ala Ser Pro Gly Phe Cys Ile Ile
        65                      70                  75                  80

Glu Gly Pro Glu Thr Val Gln Asp Phe Ala Lys Leu Asp Leu Gln Glu
                        85                  90                  95

Ile Gln Asp Asn Ile Arg Ser Arg Arg Asn Lys Ile Phe Leu His Met
                        100                 105                 110

Glu Glu Ile Arg Arg Leu Arg Ile Gln Gln Arg Ile Lys Asn Val Glu
                        115                 120                 125

Leu Gly Ile Ser Asp Glu Glu Arg Asp His Glu Leu Pro Asp Phe Pro
                        130                 135                 140

Ser Phe Ile Pro Phe Leu Pro Pro Leu Ser Ala Ala Asn Leu Lys Val
        145                     150                 155                 160

Tyr Tyr Ala Thr Cys Phe Thr Leu Ile Ala Gly Ile Met Val Phe Gly
                        165                 170                 175

Gly Phe Leu Ala Pro Ile Leu Glu Leu Lys Leu Gly Val Gly Gly Thr
                        180                 185                 190

Ser Tyr Glu Asp Phe Ile Arg Ser Val His Leu Pro Met Gln Leu Ser
                        195                 200                 205

Gln Val Asp Pro Ile Val Ala Ser Phe Ser Gly Gly Ala Val Gly Val
                        210                 215                 220

Ile Ser Ala Leu Met Val Val Glu Ile Asn Asn Val Lys Gln Gln Glu
        225                     230                 235                 240

Leu Lys Arg Cys Lys Tyr Cys Leu Gly Thr Gly Tyr Leu Ala Cys Ala
                        245                 250                 255

Arg Cys Ser Ser Thr Gly Ala Leu Val Leu Thr Glu Pro Val Ser Thr
                        260                 265                 270

Phe Ser Asp Gly Asp Gln Pro Leu Ser Ala Pro Lys Thr Glu Arg Cys
                        275                 280                 285

Pro Asn Cys Ser Gly Ser Gly Lys Val Met Cys Pro Thr Cys Leu Cys
                        290                 295                 300

Thr Gly Met Ala Met Ala Ser Glu His Asp Pro Arg Ile Asp Pro Phe
        305                     310                 315                 320

Ile

<210> SEQ ID NO 19
<211> LENGTH: 312
<212> TYPE: PRT
<213> ORGANISM: Medicago truncatula

<400> SEQUENCE: 19

Met Leu Cys Leu Gly Val Val Gly Gly Gly Ala Thr Thr Cys Leu Gln
        1               5                   10                  15

Leu Asn Asn Asn Lys Arg Phe Ile His Leu Asn Asn Lys Lys Cys Phe
                        20                  25                  30

Asn Lys Arg Trp Arg Val Met Ala Leu Glu Phe Glu Ser Asp Ser Ser
                        35                  40                  45

Ser Phe Ala Ser Ser Ile Asp Ser Asp Thr Thr Asp Lys Asn Ser
            50                  55                  60
```

```
Ala Thr Gly Phe Cys Ile Ile Glu Gly Pro Glu Thr Val Gln Asp Phe
 65                  70                  75                  80

Ala Lys Met Glu Leu Gln Ile Gln Asp Asn Ile Arg Ser Arg Arg
                 85                  90                  95

Asn Lys Ile Phe Leu His Met Glu Glu Val Arg Arg Leu Arg Ile Gln
                100                 105                 110

Gln Arg Ile Lys Asn Ala Glu Leu Gly Ile Phe Lys Glu Gln Glu
                115                 120                 125

Asn Glu Leu Pro Asn Phe Pro Ser Phe Ile Pro Phe Leu Pro Pro Leu
                130                 135                 140

Thr Ser Ala Asn Leu Arg Gln Tyr Tyr Ala Thr Cys Phe Ser Leu Ile
145                 150                 155                 160

Ser Gly Ile Ile Leu Phe Gly Gly Leu Leu Ala Pro Ser Leu Glu Leu
                165                 170                 175

Lys Leu Gly Ile Gly Gly Thr Ser Tyr Ala Asp Phe Ile Gln Asn Met
                180                 185                 190

His Leu Pro Met Gln Leu Ser Gln Val Asp Pro Ile Val Ala Ser Phe
                195                 200                 205

Ser Gly Gly Ala Val Gly Val Ile Ser Ala Leu Met Val Val Glu Ile
210                 215                 220

Asn Asn Val Lys Gln Gln Glu Gln Lys Arg Cys Lys Tyr Cys Leu Gly
225                 230                 235                 240

Thr Gly Tyr Leu Ala Cys Ala Arg Cys Ser Asn Thr Gly Ala Leu Val
                245                 250                 255

Leu Ile Glu Pro Val Ser Ser Phe Asn Gly Gly Asp Gln Pro Leu Ser
                260                 265                 270

Pro Pro Lys Thr Glu Arg Cys Ser Asn Cys Ser Gly Ser Gly Lys Val
                275                 280                 285

Met Cys Pro Thr Cys Leu Cys Thr Gly Met Ala Met Ala Ser Glu His
                290                 295                 300

Asp Pro Arg Ile Asp Pro Phe Asp
305                 310

<210> SEQ ID NO 20
<211> LENGTH: 332
<212> TYPE: PRT
<213> ORGANISM: Oryza sativa

<400> SEQUENCE: 20

Met Leu Cys Ser Ala Arg Met Leu Ala Cys Ser Gly Leu Gly Gly Pro
  1               5                  10                  15

Gly Gly Arg Leu Arg Pro Ser Pro Arg Pro Gly Ala Tyr Ala Asp Arg
                 20                  25                  30

Leu Arg Pro Pro Leu Pro Ala Arg Arg Trp Arg Val Ala Ser Ser Ala
                 35                  40                  45

Ala Ala Ser Gly Gly Ser Pro Asp Leu Pro Ser Ser Ser Ser Ser Ser
                 50                  55                  60

Ser Pro Pro Pro Thr Pro Ala Ala Ala Ser Phe Gly Ser Gly Asp Glu
 65                  70                  75                  80

Gln Ala Ala Gly Ser Pro Gly Phe Cys Ile Ile Glu Gly Pro Glu Thr
                 85                  90                  95

Val Gln Asp Phe Glu Lys Leu Asp Leu Gln Glu Ile Gln Asp Asn Ile
                100                 105                 110

Arg Ser Arg Arg Asn Lys Ile Phe Leu His Met Glu Glu Ile Arg Arg
                115                 120                 125
```

```
Leu Arg Ile Gln Gln Arg Ile Lys Asn Val Glu Leu Gly Ile Ser Val
    130                 135                 140

Asp Val Pro Glu Gly Glu Leu Pro Asp Phe Pro Ser Phe Ile Pro Phe
145                 150                 155                 160

Leu Pro Pro Leu Ser Ala Ala Asn Leu Lys Ile Tyr Tyr Ala Thr Cys
                165                 170                 175

Phe Thr Leu Ile Ala Gly Ile Met Val Phe Gly Gly Phe Leu Ala Pro
                180                 185                 190

Ile Leu Glu Leu Lys Leu Gly Val Gly Gly Thr Ser Tyr Ala Asp Phe
            195                 200                 205

Ile Arg Ser Val His Leu Pro Met Gln Leu Ser Gln Val Asp Pro Ile
        210                 215                 220

Val Ala Ser Phe Ser Gly Gly Ala Val Gly Val Ile Ser Ala Leu Met
225                 230                 235                 240

Val Val Glu Ile Asn Asn Val Lys Gln Gln Glu His Lys Arg Cys Lys
                245                 250                 255

Tyr Cys Leu Gly Thr Gly Tyr Leu Ala Cys Ala Arg Cys Ser Ser Thr
                260                 265                 270

Gly Thr Leu Val Leu Thr Glu Pro Val Ser Thr Phe Ser Asp Gly Asp
            275                 280                 285

Gln Pro Leu Ser Thr Pro Arg Thr Glu Arg Cys Pro Asn Cys Ser Gly
290                 295                 300

Ala Gly Lys Val Met Cys Pro Thr Cys Leu Cys Thr Gly Met Ala Met
305                 310                 315                 320

Ala Ser Glu His Asp Pro Arg Ile Asp Pro Phe Asp
                325                 330

<210> SEQ ID NO 21
<211> LENGTH: 320
<212> TYPE: PRT
<213> ORGANISM: Sorghum bicolor

<400> SEQUENCE: 21

Met Leu Cys Ser Gly Arg Met Leu Ala Cys Asn Gly Leu Leu Pro Gly
1               5                   10                  15

Arg Leu Arg Leu Pro Arg Ala Asp Ala Tyr Arg Leu Arg Pro Pro Ala
            20                  25                  30

Leu Ala Arg Arg Trp Ser Val Ala Ala Ser Ala Ala Ser Gly Gly
        35                  40                  45

Ser Ser Asp Leu Pro Ser Ser Ser Ser Pro Pro Thr Pro Pro Phe
50                  55                  60

Gly Val Gly Asp Asp Gln Ala Ala Ala Ser Pro Gly Phe Cys Ile Ile
65                  70                  75                  80

Glu Gly Pro Glu Thr Val Gln Asp Phe Ala Lys Leu Asp Leu Gln Glu
                85                  90                  95

Ile Gln Asp Asn Ile Arg Ser Arg Arg Asn Lys Ile Phe Leu His Met
            100                 105                 110

Glu Glu Ile Arg Arg Leu Arg Ile Gln Gln Arg Ile Lys Asn Val Glu
        115                 120                 125

Leu Gly Ile Ser Asp Glu Glu Ser Asp Arg Glu Leu Pro Asp Phe Pro
    130                 135                 140

Ser Phe Ile Pro Phe Leu Pro Pro Leu Ser Ala Ala Asn Leu Lys Val
145                 150                 155                 160

Tyr Tyr Ala Thr Cys Phe Ala Leu Ile Ala Ser Ile Met Val Phe Gly
                165                 170                 175
```

```
Gly Leu Leu Ala Pro Ile Leu Glu Leu Lys Leu Gly Leu Gly Thr
                180                 185                 190

Ser Tyr Glu Asp Phe Ile Arg Ser Val His Leu Pro Met Gln Leu Ser
            195                 200                 205

Glu Val Asp Pro Ile Val Ala Ser Phe Ser Gly Gly Ala Val Gly Val
210                 215                 220

Ile Ser Ala Leu Met Val Val Glu Ile Asn Asn Val Lys Gln Gln Glu
225                 230                 235                 240

His Lys Arg Lys Tyr Cys Leu Gly Thr Gly Tyr Leu Ala Cys Ala Arg
                245                 250                 255

Cys Ser Ser Thr Gly Ala Leu Val Leu Thr Glu Pro Val Ser Thr Phe
            260                 265                 270

Ser Asp Gly Asn Gln Pro Leu Ser Ala Pro Lys Thr Glu Arg Cys Pro
        275                 280                 285

Asn Cys Ser Gly Ser Gly Lys Val Met Cys Pro Thr Cys Leu Cys Thr
290                 295                 300

Gly Met Ala Met Ala Ser Glu His Asp Pro Arg Ile Asp Pro Phe Ile
305                 310                 315                 320

<210> SEQ ID NO 22
<211> LENGTH: 301
<212> TYPE: PRT
<213> ORGANISM: Glycine max

<400> SEQUENCE: 22

Met Leu Cys Leu Gly Arg Phe Gly Gly Val Ser His Tyr Pro Ile Lys
1               5                   10                  15

Ser Gly Trp Ser Arg Arg Asp Tyr Thr Asn Asn Arg Pro Arg Trp Cys
            20                  25                  30

Leu Met Ala Ala Gln Glu Ser Asp Ser Phe Ala Pro Ser Leu Asp
        35                  40                  45

Ser Asp Lys Thr Ala Ser Ala Gly Phe Cys Ile Ile Glu Gly Pro Glu
50                  55                  60

Thr Val Gln Asp Phe Ala Lys Met Glu Leu Gln Glu Ile Gln Asp Asn
65                  70                  75                  80

Ile Arg Ser Arg Arg Asn Lys Ile Phe Leu His Met Glu Glu Val Arg
                85                  90                  95

Arg Leu Arg Ile Gln Gln Arg Ile Lys Ser Ala Glu Leu Gly Ile Leu
            100                 105                 110

Asn Glu Glu Gln Glu Asn Glu Leu Pro Asn Phe Pro Ser Phe Ile Pro
        115                 120                 125

Phe Leu Pro Pro Leu Thr Ser Ala Asn Leu Lys Gln Tyr Tyr Ala Thr
130                 135                 140

Cys Phe Ser Leu Ile Ala Gly Ile Ile Leu Phe Gly Gly Leu Leu Ala
145                 150                 155                 160

Pro Ser Leu Glu Leu Lys Leu Gly Leu Gly Gly Thr Ser Tyr Ala Asp
                165                 170                 175

Phe Ile Glu Ser Leu His Leu Pro Met Gln Leu Ser Gln Val Asp Pro
            180                 185                 190

Ile Val Ala Ser Phe Ser Gly Gly Ala Val Gly Val Ile Ser Ala Leu
        195                 200                 205

Met Val Val Glu Ile Asn Asn Val Lys Gln Gln Glu Gln Lys Arg Cys
210                 215                 220

Lys Tyr Cys Leu Gly Thr Gly Tyr Leu Ala Cys Ala Arg Cys Ser Ser
225                 230                 235                 240
```

```
Thr Gly Ala Leu Val Leu Ile Glu Pro Val Ser Thr Val Lys Gly Gly
                245                 250                 255

Asp Lys Pro Leu Ser Pro Pro Lys Thr Glu Arg Cys Ser Asn Cys Ser
            260                 265                 270

Gly Ser Gly Lys Val Met Cys Pro Thr Cys Leu Cys Thr Gly Met Ala
        275                 280                 285

Met Ala Ser Glu His Asp Pro Arg Ile Asp Pro Phe Asp
    290                 295                 300
```

<210> SEQ ID NO 23
<211> LENGTH: 312
<212> TYPE: PRT
<213> ORGANISM: Lycopersicon esculentum

<400> SEQUENCE: 23

```
Met Val Cys Thr Gly Arg Ile Leu Ala Val Ser Tyr Ser Pro Thr Thr
1               5                   10                  15

Ser Phe His Arg Asn Tyr Arg Tyr Ser Asn Ser Arg Phe Leu Gln Gly
            20                  25                  30

Asn Leu Lys Ser Asn Leu Lys Trp Arg Ser Met Ala Ser Glu Pro Glu
        35                  40                  45

Ala Ser Ser Phe Ala Ser Ser Val Asp Ser Asp Ser Ser Asp Lys Asn
    50                  55                  60

Ser Thr Gly Phe Cys Ile Ile Glu Gly Pro Glu Thr Val Gln Asp Phe
65                  70                  75                  80

Ala Lys Met Glu Leu Gln Glu Ile Gln Asp Asn Ile Arg Ser Arg Arg
                85                  90                  95

Asn Lys Ile Phe Leu His Met Glu Glu Val Arg Arg Leu Arg Ile Gln
            100                 105                 110

Gln Arg Ile Lys Asn Ala Glu Leu Gly Ile Leu Lys Glu Glu Gln Glu
        115                 120                 125

Asn Glu Leu Pro Asn Phe Pro Ser Phe Ile Pro Phe Leu Pro Pro Leu
    130                 135                 140

Ser Ser Ala Asn Leu Lys Leu Tyr Tyr Ala Thr Cys Phe Ser Leu Ile
145                 150                 155                 160

Ala Gly Ile Ile Ile Phe Gly Gly Leu Leu Ala Pro Thr Leu Glu Leu
                165                 170                 175

Lys Leu Gly Leu Gly Gly Thr Ser Tyr Glu Asp Phe Ile Arg Ser Val
            180                 185                 190

His Leu Pro Met Gln Leu Ser Gln Val Asp Pro Ile Val Ala Ser Phe
        195                 200                 205

Ser Gly Gly Ala Val Gly Val Ile Ser Ala Leu Met Val Val Glu Ile
    210                 215                 220

Asn Asn Val Lys Gln Gln Glu Asn Lys Arg Cys Lys Tyr Cys Leu Gly
225                 230                 235                 240

Thr Gly Tyr Leu Ala Cys Ala Arg Cys Ser Ser Thr Gly Ala Leu Val
                245                 250                 255

Leu Ile Glu Pro Val Ser Thr Val Ile Ser Gly Ser Gln Pro Leu Ser
            260                 265                 270

Pro Pro Lys Thr Glu Arg Cys Ser Asn Cys Ser Gly Ala Gly Lys Val
        275                 280                 285

Met Cys Pro Thr Cys Leu Cys Thr Gly Met Gly Met Ala Ser Glu His
    290                 295                 300

Asp Pro Arg Ile Asp Pro Phe Asp
305                 310
```

<210> SEQ ID NO 24
<211> LENGTH: 1713
<212> TYPE: DNA
<213> ORGANISM: Brassica oleracea

<400> SEQUENCE: 24

```
aaaaaagtac ttccattatt tatgcaatat atactataat gctcttagta accggttaat      60
gaaagataaa aatatctctt cttcttcttc ttcgattaac aactaccatc aatctacttt     120
catctctacc accttgtcct ccgacgccgt tacaatacga tcatcactaa ttctccattg     180
tgttttgtat ttatagattt tttttctata atcagtatca tttttcataa attatcacct     240
cattcatatt cacatttatc actgaactac catcaccata gccatgaaat ctacaaacgg     300
cgttacggtc gaggcgccct catttgtatc gtaagttttt ggttatacta tactatttgg     360
acaatatgta ctatattatt tccttttgtta ctattttatt tcatatgctt catattatgt     420
actacatgca tattttgata tttgggttag aatttatatt ttttttttaa gtttagtgat     480
tagtgttttg ggtttagttt atggaaggtt tggactgacg ttgaggtaag cattacctca     540
ttcatgcaat cataagcatt tcaaaatttg aaaaatatgt actatgttat ttcgtttgtt     600
actattttat ttgataatgc ttcatattat gtactgtgtg catattttga tattagggct     660
aggatttata tagtgattag tgttttgggt ttagtttatg aaaaatttag attgacagag     720
aataagcatt acttccacta ttattaattt cattaatatg aactatacca tatgaagaat     780
gttctattct atttactctg cttatcttct tccataacat tatatctttc tccgatcatc     840
gcaatcatat taatctttgt atgaaagatg actgtttctt ttggattgac aacctctgtt     900
tcattttaa tcactcttgc cgtagtcatc atcttcgtag tctccgccac cgccggtgcg     960
ataaccaata tcaccgttct gataaccact accgccgcga ccataccgca ataatcacca    1020
caaatattga ttcaattttt tttttctttg actggcaact gccaactggt tcaaaaaag    1080
gacaaaaccg agaaaatata gcacaaatgc tatgagatct aataacttca aaattagtga    1140
catattctta atttgttggt gaaatatgac tggttcacaa ataagccctg taatattggc    1200
acatggcaaa aagaaaacta ccaagtatat ttgggtcagc atgttatcat cttatactaa    1260
taagcgcaat tgtaaaaggc ctttgcacca aggaaaatgt ttacaaaacc caccaaaaca    1320
tttaatataa ttcgacaccg cccacttatg tattttcttt tgtaaacacc tttaaagata    1380
agcatgcatg gattatccat aacaaaaaaa attcccaagt ctggaaaaaa aaaaatatcc    1440
tgccaccaca agttttatga aaacgaaatt tatttaatta aacctaccaa cactaaaaac    1500
aagtgtaaaa taaacaaata caacaaccag taaaatctcg ccacgtacaa aaactacagt    1560
tcgtaataga gtgtggtggt ctctctctct ctctcggtct cgatttctga tttctgattc    1620
ctcactgtac gaccaaaact aaaccacact gacagacaca cataaaagaa caggcaaact    1680
aattgatccg ctgctgaaga tctcgaaacc atg                                 1713
```

<210> SEQ ID NO 25
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature

```
-continued
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 25

Cys Xaa Xaa Cys Xaa Gly Xaa Gly
1               5
```

US 8,138,391 B1

OR GENE AND ITS USE IN MANIPULATING CAROTENOID CONTENT AND COMPOSITION IN PLANTS AND OTHER ORGANISMS

BACKGROUND OF THE INVENTION

1. Field of the Invention

This invention relates to a gene, the Or gene, cloned from an orange cauliflower mutant, a construct containing the gene and its promoter, a vector and method of transforming plants utilizing the construct and vector, and plants transformed with the gene construct.

2. Description of the Relevant Art

Carotenoids are a diverse group of pigments widely distributed in nature. They are synthesized de novo in all photosynthetic organisms, as well as in some non-photosynthetic bacteria and fungi (Goodwin and Britton. 1988. In: *Plant Pigments*, Goodwin, T. W., ed., Academic Press, London, pages 61-132). Carotenoids fulfill many essential functions in plants (Demmig-Adams and Adams. 1996. *Trends Plant Sci.* 1: 21-26; Frank and Cogdell. 1996. *Photochem Photobiol.* 63: 257-264; Yamamoto et al. 1997. *Photochem Photobiol.* 65: 62S; Niyogi, K. K. 1999. *Annu. Rev. Plant Physiol. Plant Mol. Biol.* 50: 333-359; Ma et al. 2003. *Proc. Natl. Acad. Sci. USA* 100: 4377-4382). They play important roles in human nutrition and health as the primary source of dietary provitamin A (Combs, G. F. Jr. 1998. *The Vitamins: Fundamental Aspects in Nutrition and Health*, 2$^{nd}$ Edition, Academic Press, San Diego) and in reducing risks of cancers and other chronic diseases (Mayne, S. T. 1996. *FASEB J.* 10: 690-701; Smith-Timothy, A. D. 1998. *British J. Biomed. Sci.* 55: 268-275; Giovannucci, E. 1999. *J. Natl. Cancer Inst.* 91: 317-331; Bertram, J. S. 1999. Nutr. Rev. 57: 182-191; Palace et al. 1999. *Free Radical Biol. Med.* 26: 746-761).

Carotenoid biosynthesis is a multifaceted and highly regulated process in plants (Hirschberg, J. 2001. *Curr. Opin. Plant Biol.* 4: 210-218; Bramley, P. M. 2002. *J. Exp. Bot.* 53: 2107-2113). Exciting progress has been made in identifying and characterizing genes encoding enzymes for the biosynthesis of carotenoids in plants (Cunningham and Gantt. 1998. *Annu. Rev. Plant Physiol. Plant Mol. Biol.* 49: 557-583; Hirschberg, supra; Fraser and Bramley. 2004. *Prog. Lipid Res.* 43: 228-265). Comparatively, little is known about the regulatory mechanisms underlying carotenoid accumulation and/or the signal pathways that trigger the differentiation of plastids into chromoplasts.

To gain new insights into the molecular control of carotenogenesis in plants, we are studying the Or gene in cauliflower (*Brassica oleracea* var. *botrytis*). The cauliflower Or gene arose as a result of spontaneous mutation. It causes many low-pigmented tissues of the plant, most noticeably the edible curd and shoot, to accumulate carotenoids (Crisp et al. 1975. *Euphytica* 24: 173-176; Dickson et al. 1988. *Hortscience* 23: 778-779; Li et al. 2001. *Plant J.* 26: 59-67) (FIG. 1). Our previous studies showed that the predominant carotenoid that accumulated in the affected tissues is beta-carotene, which can reach levels of several hundred fold higher than those found in the comparable tissues of wild type cauliflower (Li et al., supra). The Or gene appears not to exert its effect via the direct regulation of carotenogenic gene expression. Therefore it represents a novel carotenoid gene mutation. Such carotenoid mutants can provide useful tools for exploring the regulation of carotenoid accumulation.

The indispensable role of carotenoids in plants and the increasing interest in their health benefits to humans have prompted a significant effort to understand carotenoid biosynthesis in plants. Although major genes and their biochemical roles in carotenogenesis have been well documented, the control mechanisms regulating the overall carotenoid biosynthesis remain an enigma (Cunningham and Gantt, Hirschberg Fraser and Bramley, supra). Only a few gene mutations are known to induce carotenoid accumulation in unpigmented tissues (Crisp et al., supra; Buishand and Gabelman. 1979. *Euphytica* 28: 611-632). The high-beta-carotene Or (Orange) gene mutation in cauliflower provides us an ideal model to divulge the regulatory control as it switches on carotenogenesis in tissues where the activity of this pathway is normally repressed (Li et al., 2001, supra).

Because of the important role of carotenoids in plants and their beneficial effects for humans and animals, knowing the determinants of carotenoid accumulation could provide a novel and powerful tool, along with the catalytic genes, to enrich carotenoids in important food crops. Increasing provitamin A content in staple crops such as rice and wheat helps in the alleviation of the global incidence of vitamin A deficiency, a condition which affects several million people worldwide and results in blindness, poor immune function, and early death. Furthermore, the Or gene could be used to alter food plants to selectively modify carotenoid content and/or composition to provide protection against certain other diseases, thus improving various aspects of human well being and reducing the economic costs associated with these diseases. Additional uses for the Or gene include its use to impart novel color variation in plants, and to provide feed additives in animal feeds. Therefore, it is a primary object of this invention to provide a molecular tool and method for increasing accumulation of carotenoids in cells.

SUMMARY OF THE INVENTION

We have expressed the isolated Or gene from the cauliflower mutant plant in both white cauliflower and *Arabidopsis* and confirmed that its expression results in the induction of carotenoid biosynthesis in the transformed plants.

In accordance with this discovery, it is an object of the invention to provide an isolated nucleic acid construct containing a DNA sequence which encodes the Or protein involved in the regulation of carotenoid accumulation in plants.

It is a further object of the invention to provide a vector which comprises a construct which is capable of expressing the Or gene.

It is a still further object of the invention to provide a host cell comprising the vector capable of expressing the Or gene.

It is an additional object of the invention to provide transgenic plants, plant cells, and seeds containing the nucleic acid construct.

It is a another object of the invention to provide a method of transforming the Or gene into plants by administering a vector, wherein said vector comprises an effective amount of a nucleic acid construct, which is a DNA sequence which is capable of transforming the Or gene into a plant and observing that said administration of the vector is effective for inducing carotenoid biosynthesis in said plant.

It is yet another object of the invention to provide a method of manipulating carotenoid content in plants by stably transforming a plant with an isolated nucleotide molecule capable of modulating carotenoid content, operably linked with a promoter capable of driving expression of a gene in a plant cell.

It is yet another object of the invention to provide plants, plant cells, and plant parts, that have been transformed by the Or gene-containing construct of the invention and comprising enhanced carotenoid content when compared to plants of the same species which have not been transformed.

Other objects and advantages of this invention will become readily apparent from the ensuing description.

BRIEF DESCRIPTION OF THE DRAWINGS

The patent or application file contains at least one drawing executed in color, Copies of this patent or patent application publication with color drawing(s) will be provided by the U.S. Patent and Trademark Office upon request and payment of the necessary fee.

FIGS. 1A-1D depict the effect of the Or gene mutation on the curd and the shoot of cauliflower; Panels 1A and 1C reflect expression of or/or, Panels 1B and 1D, Or/Or.

FIG. 3 shows the DNA sequence alignment of the wild type or gene (SEQ ID NO:2) with the Or allele genomic DNA (SEQ ID NO:1).

FIG. 4A shows the cDNA sequence alignment of the wild type or and the mutant Or variants, Or-I, Or-D1, and Or-D2. FIG. 4 B shows the amino acid sequence alignment of the wild type or protein with the mutant Or variants, Or-I, Or-D1, and Or-D2.

FIGS. 10A-D shows the subcellular localization of the or protein in the plant: or-GFP in leaves (FIG. 10A) and seeds (FIG. 10C); vector in leaves (FIG. 10B) and seeds (FIG. 10D).

FIGS. 12A-C depict increased carotenoid accumulation in transgenic *Arabidopsis*. FIG. 12A shows the transgenic *Arabidopsis*. FIG. 12B shows HPLC elution profiles of pigments from inflorescence meristems of the *Arabidopsis* transformants. The elution profile of pBAR1 was shifted for easy comparison. FIG. 12C depicts the total concentration of carotenoid in inflorescence meristems of the transgenic lines.

DETAILED DESCRIPTION OF THE INVENTION

Figure 2:
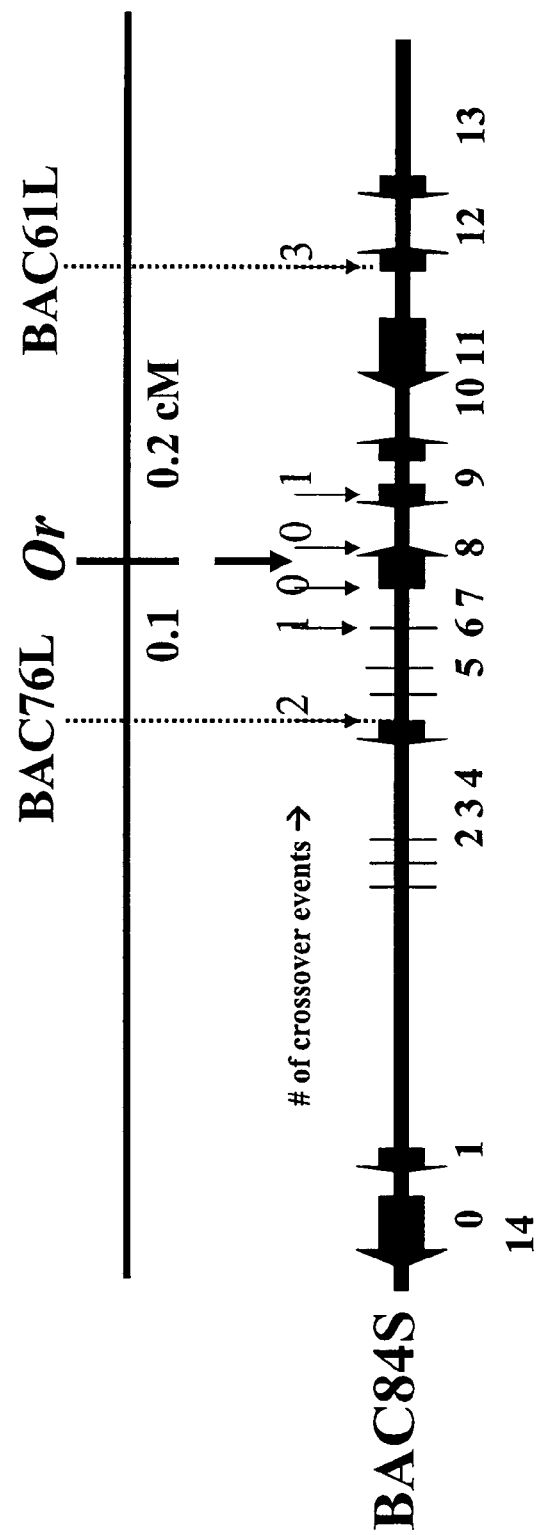
FIG. 2 shows the identification of a single gene as the Or candidate gene.

This invention concerns the isolation of the Or gene, a gene involved in carotenoid accumulation in low-pigmented tissues of plants; the cloning and functional analysis of the Or gene in cauliflower; and the transformation of an additional plant, *Arabidopsis*, with nucleic acid encoding the Or protein. Using the compositions and methods of the invention, plant cells are genetically manipulated resulting in enhanced accumulation of carotenoids in plant cells and tissues. The nucleic acid molecules, constructs and vectors of the invention and the methods of using them can be utilized to increase carotenoid levels in important food crops. The Or gene represents the first identified regulatory gene serving as a controlling switch of the carotenoid accumulation in specific tissues of the plant, perhaps through involvement in the differentiation of non-photosynthetic plastids into chromoplasts. The Or protein is a DnaJ-like plastid membrane protein which mediates enhanced carotenoid accumulation in cauliflower and other plants; the Or protein exists in alternative forms, e.g., Or-I, Or-D1, and Or-D2.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" refers to a nucleic acid sequence encoding a protein, here the Or protein, operably linked to a promoter and/or other regulatory sequences.

As used herein, the term "express" or "expression" is defined to mean transcription alone. The regulatory elements are operably linked to the coding sequence of the Or gene such that the regulatory element is capable of controlling expression of Or gene. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, as for example, the promoter disclosed here which specifically induces the Or gene expression in apical meristems, inflorescence meristems; callus, and flower tissues, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence (described above) which specifically induces the Or gene expression in apical meristems, inflorescence meristems, callus, and flower tissues. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143:277) and particle-accelerated or "gene gun" transformation technology (Klein et al. 1987. *Nature (London)* 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one Or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The term "substantially pure" as used herein refers to Or polypeptide that is substantially free of other proteins, lipids, carbohydrates or other materials with which it is naturally associated. One skilled in the art can purify Or using standard techniques for protein purification. The purity of the Or polypeptide can also be determined by amino-terminal amino acid sequence analysis.

The invention includes functional Or polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of Or polypeptide", refers to all fragments of Or that retain Or activity and function in the carotenoid accumulation pathway. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of Or in the carotenoid accumulation pathway can be utilized in bioassays to identify functional fragments of Or polypeptide or related polypeptides.

Modifications of the Or primary amino acid sequence may result in further mutant or variant proteins having substantially equivalent activity to the Or polypeptides described herein. Such modifications may be deliberate, as by site-directed mutagenesis, or may occur by spontaneous changes in amino acid sequences where these changes produce modified polypeptides having substantially equivalent activity to the Or polypeptides. Any polypeptides produced by minor modifications of the Or primary amino acid sequence are included herein as long as the biological activity of Or is present; e.g., having a role in pathways leading to carotenoid accumulation in plants.

A heterologous coding sequence refers to coding sequences which encode peptides or proteins, unrelated to, or, other than, the Or polypeptides provided above and which are not intrinsically found in the position provided in the chimeric gene construct.

Genes encoding an Or protein can be cloned using a variety of techniques according to the invention. The simplest procedure for the cloning of Or genes requires the cloning of genomic DNA from an organism identified as producing an Or protein, and the transfer of the cloned DNA on a suitable plasmid or vector to a host organism which does not produce the Or protein, followed by the identification of transformed hosts to which the ability to produce the Or protein has been conferred. The transforming Or-conferring DNA can be cleaved into smaller fragments and the smallest which maintains the Or-conferring ability can be further characterized. Techniques suitable for cloning by homology include standard library screening by DNA hybridization or polymerase chain reaction (PCR) amplification using primers derived from conserved sequences. As defined herein, two DNA sequences are substantially homologous when at least 80% (preferably at least 85% and most preferably 90%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. Nucleic Acid Hybridization, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a Or polypeptide and which hybridize under stringent conditions to the Or sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Unless otherwise indicated, sequence alignments and percent identity calculations were performed using the Megalign program of the LASERGENE bioinformatics computing suite (DNASTAR Inc., Madison, Wis.), or any equivalent program. Multiple alignment of the sequences was performed using the Clustal W method of alignment (Higgins and Sharp (1989. *CABIOS* 5:151-153) with the default parameters (GAP PENALTY=10, GAP LENGTH PENALTY=1.0), while default parameters for pairwise alignments using the Clustal W method were GAP PENALTY=10, GAP LENGTH PENALTY=1.0, Slow-Accurate unless otherwise indicated.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. J. Mol. Biol. 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. For example, that portion of the Or protein beginning with amino acid 60, i.e., glycine, and consisting of 246 contiguous amino acids or less (as described above), can be used to identify or isolate the Or gene encoding said Or protein in nucleotide sequences of plants other than cauliflower. Thus, such a portion represents a "substantial portion" and can be used to establish "substantial identity", i.e., sequence identity of at least 80%, compared to the reference sequence, cauliflower. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended.

Fragments of a nucleotide sequence may encode protein fragments that retain the biological activity of the native protein and hence have Or-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the Or polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, Or activity as described herein. Such variants may result from, for example, genetic polymorphism or from human manipulation. Biologically active variants of a native Or protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired Or activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of Or protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

Figure 3:
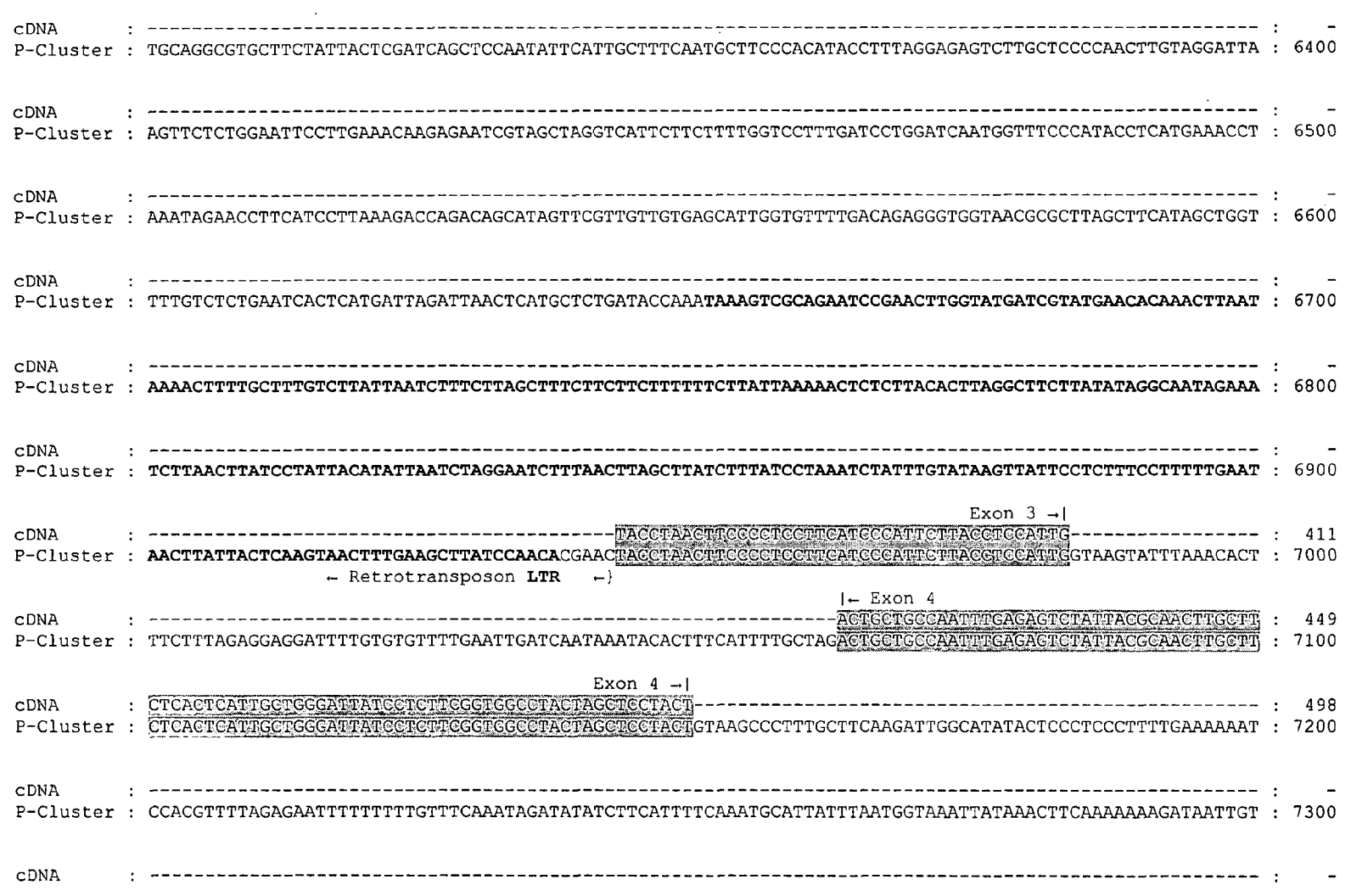

The Or gene of the invention has been identified and cloned by using a map-based cloning strategy. To isolate the Or gene via positional cloning, markers closely linked to Or (Li and Garvin. 2003. *Genome* 46: 588-594) were identified and the Or locus was delimited to a genetic and physical interval of 0.3 cM and 50 kb, respectively, within a single bacterial artificial chromosome (BAC) vector (Li et al. 2003. *Mol. Gen. Genomics* 270: 132-138). Fine mapping identified only one gene that cosegregated with the Or locus (FIG. 2). Sequence comparison of this gene from the WT and the Or mutant revealed a 4.4-kb retrotransposon insertion in the mutant (FIG. 3). Thus, fine genetic mapping, along with a large insertion in the mutant allele, unequivocally defined a single candidate gene for Or.

Alignment of the WT cDNA with the genomic sequence defined a gene structure with 8 exons and 7 introns. The insertion of the retrotransposon in the Or allele occurred in exon 3 between the putative transit peptide and the first transmembrane domain. The open reading frame of this gene, consists of 915 nucleotides (SEQ ID NO: 2) and is predicted to encode a protein of 305 amino acids (SEQ ID NO:7) with an estimated molecular mass of 33.5 kDa. The protein contains a tandem cysteine-rich repeat, showing an atypical zinc finger domain of DnaJ protein.

Figure 4A:
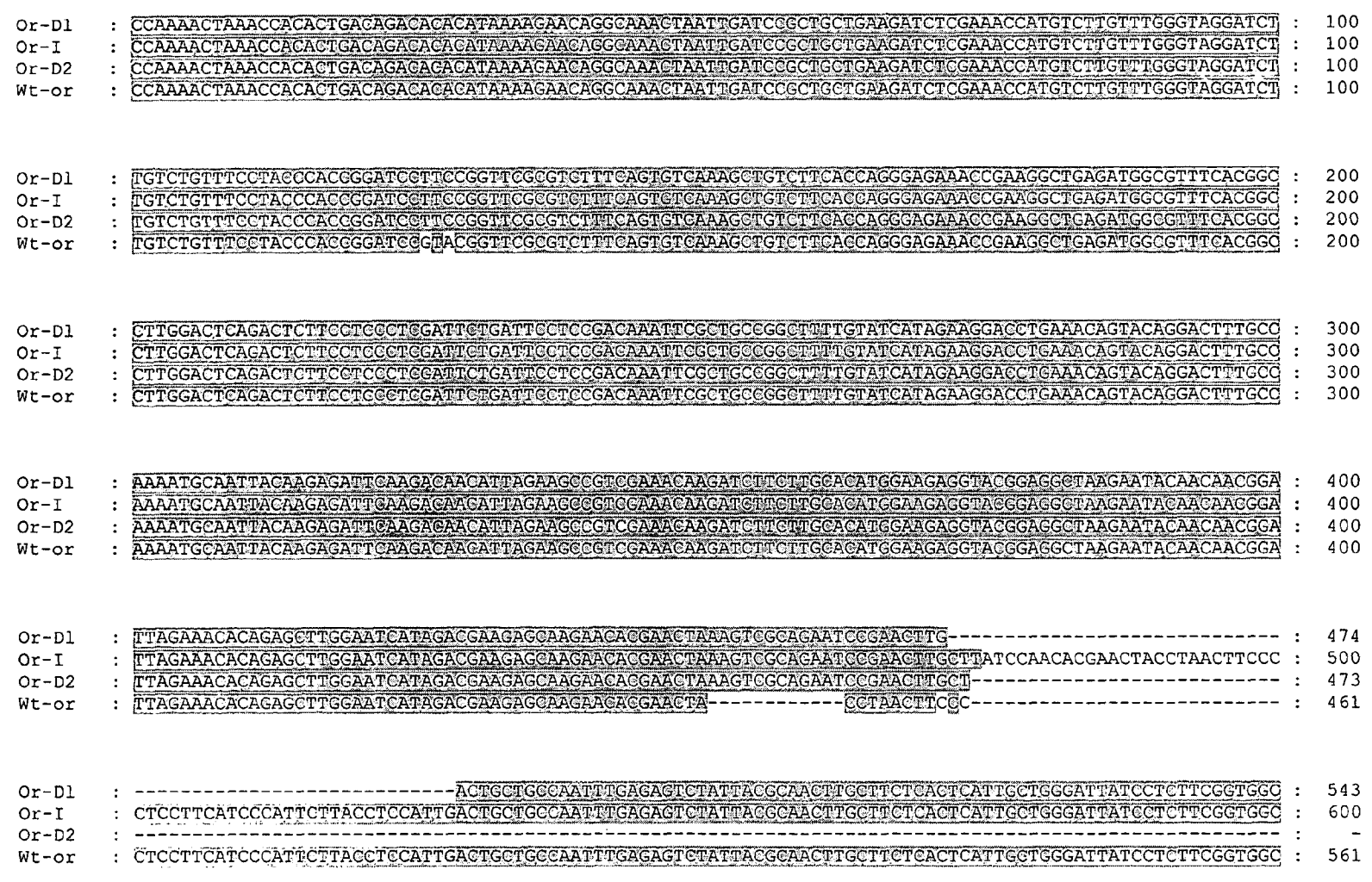
Figure 4A:
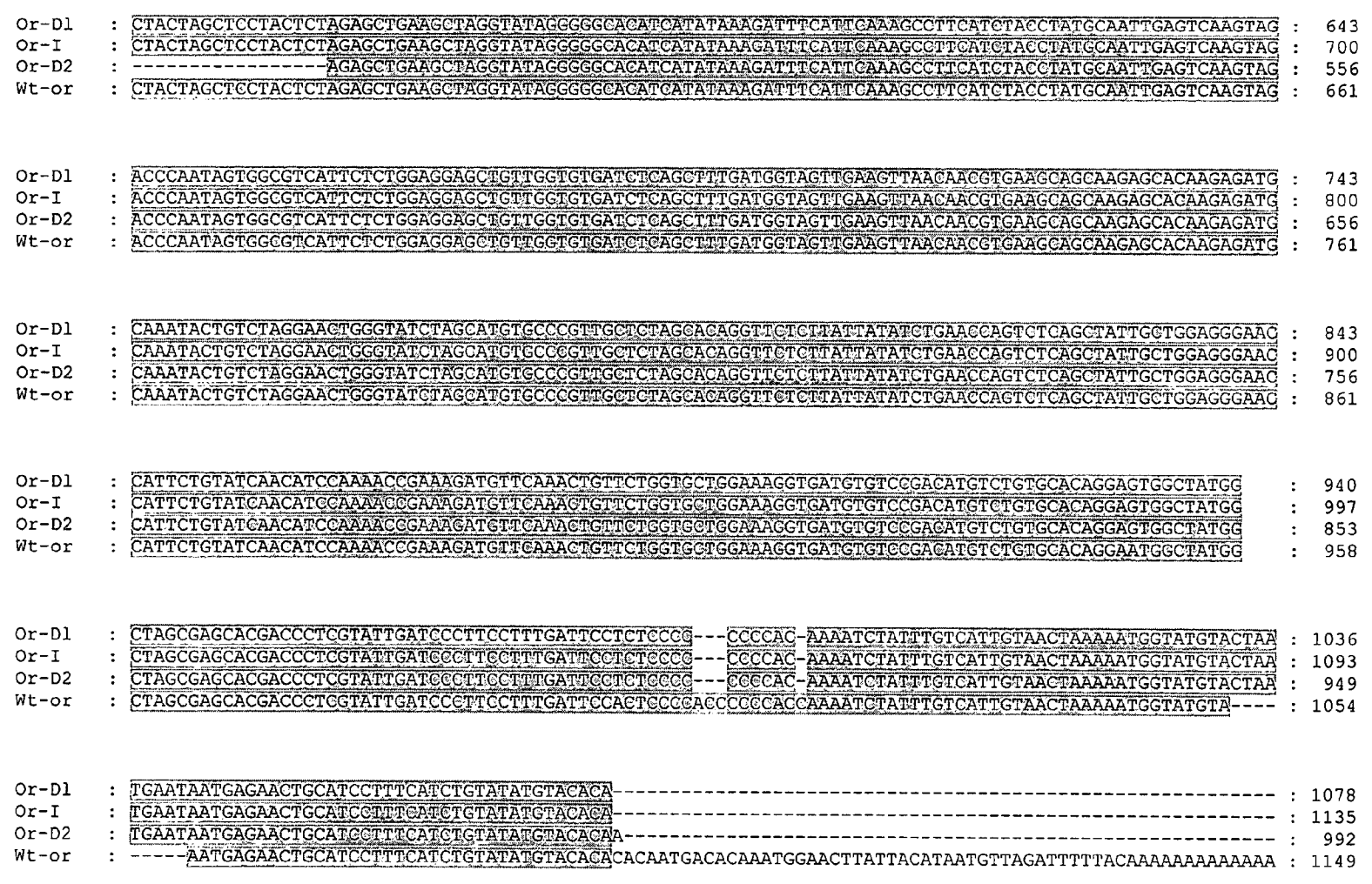
Figure 4B:
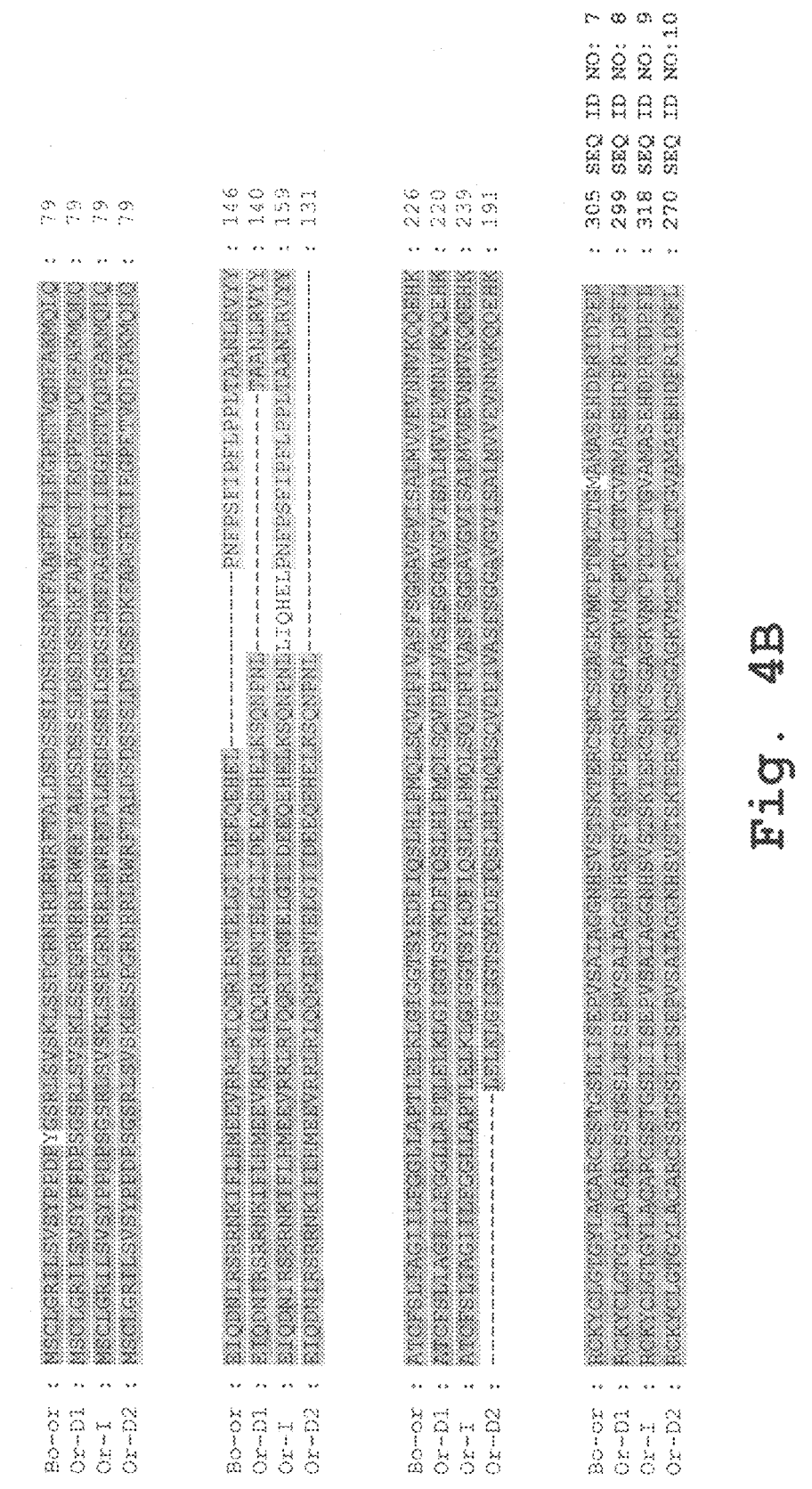

Sequencing the full-length cDNA clones from curd tissue of the mutant revealed the existence of alternative splicing events. These alternatively spliced transcripts were also detected in leaf tissue of the Or mutant, although carotenoid content and composition appear not disturbed by Or. Three major alternatively spliced transcripts were cloned: the Or-I transcript (SEQ ID NO: 5) having a 39 bp insertion and two transcripts having deletions (Or-D1 and Or-D2; SEQ ID NO:4 and SEQ ID NO:6, respectively). PCR analysis of the Or mutant cDNA pool revealed that the Or-D1 was the most abundant. The predicted protein resulting from the insertion (SEQ ID NO: 9) contains 13 new amino acids (KSQNPN-LLIQHEL; SEQ ID NO:11) and the predicted protein resulting from the two deletions Or-D1 and Or-D2 (SEQ ID NOs: 8 and 10, respectively) have 7 new amino acids (KSQNPNL; SEQ ID NO:12) with a deletion of 13 and 42 amino acids, respectively, from the WT protein (FIG. 4). All of them utilize the original stop codon for translation. The Or-D1 is the most abundant transcript and only a small size difference exists between the Or variants and WT or transcript, indicating similar size of transcripts for WT and the mutant. A comparable abundance of transcripts was observed in the curds, flowers, and very young leaves of WT and the mutant. No WT or transcript was found from sequencing more than 40 clones isolated from the mutant cDNA pool, and vice versa.

BLAST searches showed that Or encodes a protein that contains a cysteine-rich Zn-binding domain in DnaJ-like proteins. Or orthologs with significant high sequence homology were found in many plant species including *Arabidopsis*, tomato, maize, and rice etc. Searching the DNA microarray expression databases revealed that the *Arabidopsis* Or ortholog expresses mainly in meristem tissues, and that of the tomato, in flowers and developing fruits, which agrees well with the general Or expression pattern in cauliflower. Amino acid sequence comparison of putative Or homologs from different plants showed that Or contains two transmembrane domains and a conserved atypical DnaJ zinc figure (Cxx-CxGxG; SEQ ID NO:25)4 motif, presumably to be involved in protein-protein interaction. The striking sequence conservation of these domains suggest their crucial role for Or function.

To confirm the identity of the Or candidate gene, a 9.2-kb genomic fragment containing only the Or gene and the retrotransposon with 1.7 kb upstream and 1.0 kb downstream of the gene was inserted into pBAR1 binary vector to produce pBAR1-Or construct. The construct and vector were individually electroporated into *Agrobacterium tumefaciens* strain LBA4404 and transformed into *Arabidopsis thaliana* ap1-1/cal-1 homozygous mutant using a floral dipping method (Clough and Bent. 1998. *Plant J.* 16: 735-743), and into cauliflower wild type hypocotyl explants essentially following the methods described by Metz et al. (1995. *Plant Cell Rep.* 15: 287-292). The positive transformants were confirmed by PCR amplification of the selective markers. As expected, cauliflower curds and the *Arabidopsis* ap1-1/cal-1 influorescence meristems with distinct orange color were formed in the pBAR1-Or transformants. Carotenoids were extracted and analyzed. HPLC analysis confirmed that the color change is due to carotenoid accumulation. The successful phenotypic complementation of Or in the *Arabidopsis* mutant provides strong evidence that Or can work across species to enhance carotenoid accumulation.

To determine whether Or is a dominant negative or a gain-of-function mutant, over 30 independent double-stranded RNA (dsRNA) transgenic lines were generated in cauliflower. The resulting transformants showed reduced or undetectable levels of Or transcripts when compared to controls. Examination of the dsRNA transgenic lines revealed no observed mutant phenotype or increased level of carotenoid accumulation. The results suggest that Or is likely a gain-of-function mutation that positively controls carotenoid accumulation.

Carotenoids are synthesized exclusively in plastids in plants. The entire coding region of the wild type or gene was fused to a modified green fluorescent protein (GFP) gene under the control of 35S promoter and the construct was used to transform *Arabidopsis*. Or-GFP appeared not to be expressed in the fully developed chloroplasts of leaves, but expressed predominantly in epidermal cells in the leucoplasts which are the main plastid found in WT cauliflower curds. Immunoblot analysis of proteins from the purified chromoplasts or leucoplasts demonstrated the association of Or protein with these plastids, confirming plastid localization.

The cauliflower Or gene apparently represents a previously uncharacterized class of regulatory genes that control carotenoid accumulation in low-pigmented tissues of plants. The specific mechanism of Or-induced carotenoid accumulation has yet to be fully elucidated and a multitude of possibilities still exist. Carotenoid accumulation represents a steady state of biosynthesis, degradation and sequestration. Factors influencing each of these processes directly affect carotenoid accumulation, thus providing many hypothetical points. For example, although our preliminary studies suggest that Or does not directly upregulate flux through the carotenoid pathway (data not shown), the Or gene could regulate carotenoid enzyme complex association for their biological function. In a previous report, a Hsp 70 has been shown to be associated with a soluble form of phytoene desaturase in a large protein complex and resulted in down-regulation of carotenogenic activity (Al Babili et al. 1996. *Plant J.* 9: 601-612). The likely gain-of-function Or protein may promote the formation of functional enzyme complex to maximally activate the pathway. Further, the Or gene could exert its effect on carotenoid accumulation by altering a process controlling the catalytic activity of the carotenoid pathway. However, we believe that our collective results are suggestive of the possibility that the Or gene may cause carotenoid accumulation by being involved in the differentiation of non-photosynthetic plastids into chromoplasts, which in turn provide a metabolic sink that effectively sequesters the end products in creating a chemical dis-equilibrium to drive carotenoid synthesis to a completion (Rabbani et al. 1998. *Plant Physiol.* 116: 1239-1248; Vishnevetsky et al. 1999. *Trend Plant Sci.* 4: 232-235).

In plants, chromoplasts are derived from chloroplasts, proplastids and other non-photosynthetic plastids, as seen in carrot and squash (Marano et al. 1993. *Plant Sci.* 94: 1-17). The hypothesis that Or likely involves in the metabolic processes that controls the differentiation and/or division of the non-photosynthetic plastids into chromoplasts will accommodate the following observations. First, Or expresses highly in tissues originated with large quantity of non-photosynthetic plastids. Second, the Or mutant resembles chloroplast division mutants of ARC6 (Pyke et al. 1994. *Plant Physiol.* 106: 1169-1177) in containing one or two large chromoplasts in each cell of the mutant tissues (Li et al., 2001, supra). Recently, it has been shown that the ARC6 gene also encodes a DnaJ-like plastid protein in the assembly and/or stabilization of the key plastid division protein FtsZ ring (Vitha et al. 2003. *Plant Cell* 15: 1918-1933). Identification of proteins which directly interact with Or would provide new insight into the functional role of Or in regulation of carotenoid accumulation in the plant.

The successful cloning of Or is a major step in our understanding of the regulatory mechanisms underlying carotenoid accumulation in plants. Deciphering the mechanism by which this gene functions to result in the mass accumulation of carotenoids will aid in devising new strategies and/or control points for improving carotenoid contents in crops.

EXAMPLES

Having now generally described this invention, the same will be better understood by reference to certain specific examples, which are included herein only to further illustrate the invention and are not intended to limit the scope of the invention as defined by the claims.

Example 1

Plant Materials

The cauliflower varieties used in this study include a wild type (WT, genotype oror) cultivar "Stovepipe", and a homozygous mutant (Or, genotype OrOr) line "1227". Heterozygous plants (Oror) were produced from a cross between these two cultivars. Plants were grown in a greenhouse at 20° C. with 14 h/10 h light dark regime. Leaf and curd samples for RNA and DNA extraction as well as for HPLC analysis were harvested, frozen in liquid nitrogen, and stored at −80° C. until use.

Example 2

Nucleic Acid Analysis

Total genomic DNA was isolated from leaf tissues of cauliflower plants either following the method of Riede and Anderson (1996. *Crop Sci.* 36: 905-909) or by a modified minipreparation according to Dellaporta et al. (1983. *Plant Mol. Biol. Rep.* 1: 19-21). Genomic DNA was digested with restriction enzymes, separated on 0.8% agarose gels, and blotted onto Hybond N+ membranes (Amersham). Probes were radiolabeled by the method of Feinburg and Vogelstein (1984. *Anal. Biochem.* 137: 266-267). Pre-hybridization, hybridization, and washing of the membranes were conducted as previously described (Li and Garvin, supra).

Total RNA was extracted using Trizol reagent (Invitrogen). For Northern blot analysis, RNA samples (20 µg each) were separated on a formaldehyde agarose gel and transferred onto Hybond N+ membrane (Amersham). Equal loading of the samples were monitored by ethidium bromide stained gel, and verified by probing the blot with actin or 18 s rRNA. The probe for Or was the cDNA fragment encoding the putative transit peptide for higher specificity. Membranes were hybridized in UltraHyb (Ambion) overnight and washed at 42° C. for 2×5 min, in 2×SSC and 0.1% (w/v) SDS, followed by at 42° C. for 2×15 min, in 0.1×SSC and 0.1% (w/v) SDS. The membranes were exposed to X-ray film (Kodak BioMax) for 1-3 days or to phosphorimager screen and then scanned by Storm 860 (Amersham).

Example 3

Identification of a Single Candidate Gene for Or

Previously, we identified a single BAC harboring the Or locus (Li et al., supra). The entire BAC clone (BAC84S) was sequenced by MWG sequencing service (High Point, N.C.) and fifteen putative genes were identified based on the computer program of GENSCAN (http://genes.mit.edu/GENSCAN.html) (FIG. 2). The F2 recombinant plants were used for fine mapping to identify candidate genes cosegregating with Or. Fine mapping of the putative genes between BAC76L and BAC61 L marker sequences identified only one gene that cosegregated with the Or locus. Sequence comparison of this gene from the WT and the Or mutant revealed a 4.4-kb retrotransposon insertion in the mutant (FIG. 3). Thus, fine genetic mapping, along with a large insertion in the mutant allele, unequivocally defined a single candidate gene for Or.

Example 4

Confirmation of the Identity of the Or Candidate Gene by Phenotypic Complementation in WT Cauliflower To confirm the identity of the Or candidate gene, a 9.2-kb genomic fragment containing only the candidate gene with 1.7 kb upstream and 1.0 kb downstream of the gene and the retrotransposon insertion was cloned into pBAR1 binary vector to produce pBAR1-Or construct. To make a double-stranded RNAi construct for specifically silencing this gene, a 450-bp fragment of the or gene in antisense and sense orientations were constructed into the binary vector pFGC5941 (obtained from TAIR; http://www.arabidopsis.org/).

Figure 5:
FIG. 5 depicts complementation of the "orange" phenotype by the Or gene in cauliflower. The color of the cauliflower on the left reflects transformation with the pBAR1 vector, that on the right shows the effect of pBAR1-Or transformation.

The constructs and vectors were individually electroporated into *Agrobacterium tumefaciens* strain LBA4404 and transformed into Arabidopsis thaliana ap1-1/cal-1 homozygous mutant using a floral dipping method (Clough and Bent. 1998. *Plant J.* 16: 735-743), and into cauliflower wild type hypocotyl explants essentially following the methods described by Metz et al. (1995. *Plant Cell Rep.*15: 287-292). The positive transformants were confirmed by PCR amplification of the selective markers. As expected, curds with distinct orange color were formed in the pBAR1-Or transformants (FIG. 5).

Carotenoids were extracted and analyzed following the method as described (Li et al., 2001, supra). HPLC analysis confirmed that the color change is due to carotenoid accumulation (data not shown). Quantification was carried out using a calibration curve generated with a commercially available beta-carotene standard (Sigma).

Figure 6:
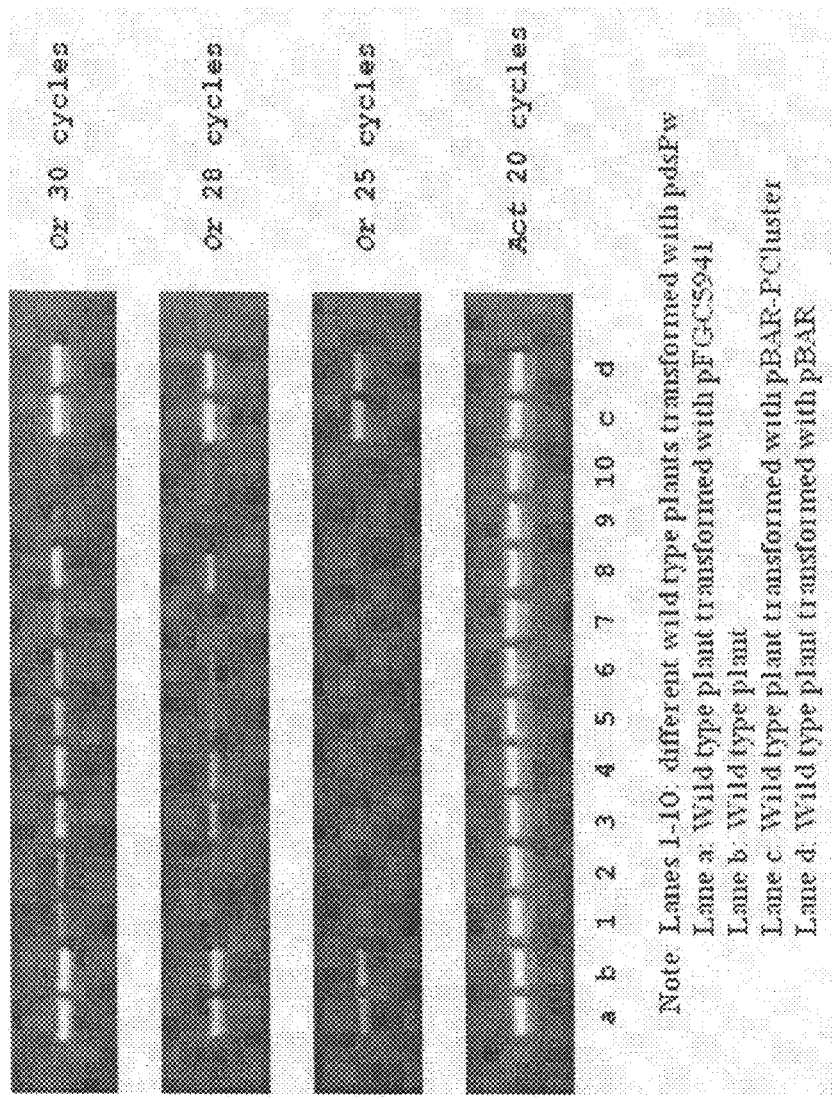
FIG. 6 shows expression of Or transcripts in transgenic cauliflower plants.

To obtain clues on whether Or is a dominant negative or a gain-of-function mutant, we generated over 30 independent double-stranded RNA (dsRNA) transgenic lines in cauliflower. In comparison to controls, these transformants showed reduced or undetectable levels of Or transcripts (FIG. 6). Examination of the dsRNA transgenic lines revealed no observed mutant phenotype or increased level of carotenoid accumulation (data not shown). The results suggest that Or is likely a gain-of-function mutation that positively controls carotenoid accumulation.

Example 5

Structure of the Or Gene

Figure 7:
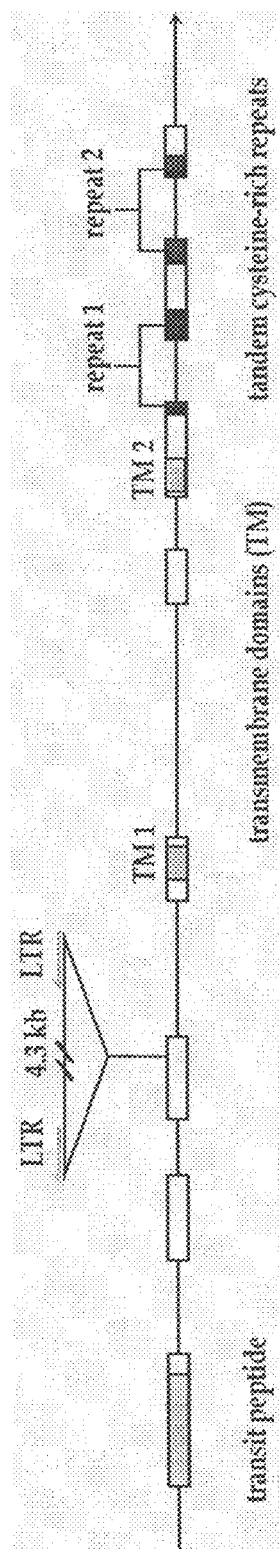
FIG. 7 depicts the structure of the Or allele.

To isolate the full-length cDNA sequences from both the wild type and the Or mutant, primers were designed based on the gene sequence and used to clone the full-length cDNA through 5' and 3' rapid amplification of cDNA ends (RACE) procedure (Smart RACE cDNA Amplification Kit, Clontech). Full-length cDNAs were then amplified from cDNA pools of wild type and mutant using 5' and 3' end sequence primers with Pfu Ultra DNA polymerase (Stratagene), subcloned into pCR-Blunt-II vector (Invitrogen) and sequenced. Sequences were searched against GenBank database, and analyzed with various web-based software packages (e.g., BLAST). Alignment of the WT cDNA with the genomic sequence defined a gene structure with 8 exons and 7 introns. The insertion of the retrotransposon in the Or allele occurred in exon 3 between the putative transit peptide and the first transmembrane domain (FIG. 7). The open reading frame of this gene consists of 918 nucleotides and is predicted to encode a protein of 305 amino acids with an estimated molecular mass of 33.5 kDa. This protein contains two transmembrane helices (http://www.cbs.dtu.dk/services/TM-HMM-2.0/) and was predicted (http://www.cbs.dtu.dk/services/TargetP/) for a plastid localization. It contains a tandem cysteine-rich repeat, showing an atypical zinc finger domain of DnaJ protein.

Figure 8:
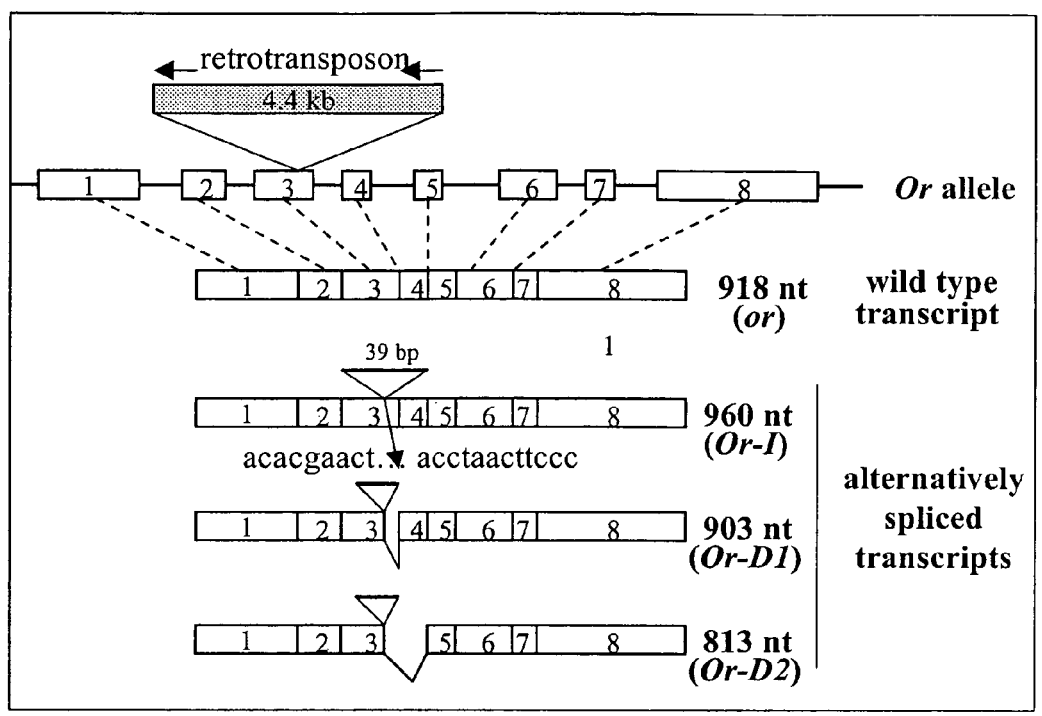
FIG. 8 depicts alternatively spliced transcripts related to the wild type or transcript.

Sequencing the full-length cDNA clones from curd tissue of the mutant revealed the existence of alternative splicing events (FIG. 8). These alternatively spliced transcripts were also detected in leaf tissue of the Or mutant, although carotenoid content and composition appear not disturbed by Or. Three major alternatively spliced transcripts were cloned: the Or-1 transcript (SEQ ID NO: 5) having a 39 bp insertion and two transcripts having deletions (Or-D1 and Or-D2; SEQ ID NO:4 and SEQ ID NO:6, respectively). PCR analysis of the Or mutant cDNA pool using primers closer to splicing site revealed that the Or-D1 was the most abundant one (data not shown). The predicted proteins from the insertion (SEQ ID NO: 9) contains 13 new amino acids (KSQNPNLLIQHEL; SEQ ID NO:11) and the predicted protein resulting from the two deletions Or-D1 and Or-D2 (SEQ ID NOs: 8 and 10, respectively) have 7 new amino acids (KSQNPNL; SEQ ID NO:12) with a deletion of 13 and 42 amino acids, respectively, from the WT protein (FIG. 4). All of them utilize the original stop codon for translation (FIG. 8). No WT or transcript was found from sequencing more than 40 clones isolated from the mutant cDNA pool, and vice versa.

Example 6

Molecular Characterization of the Or Gene

Figure 9:
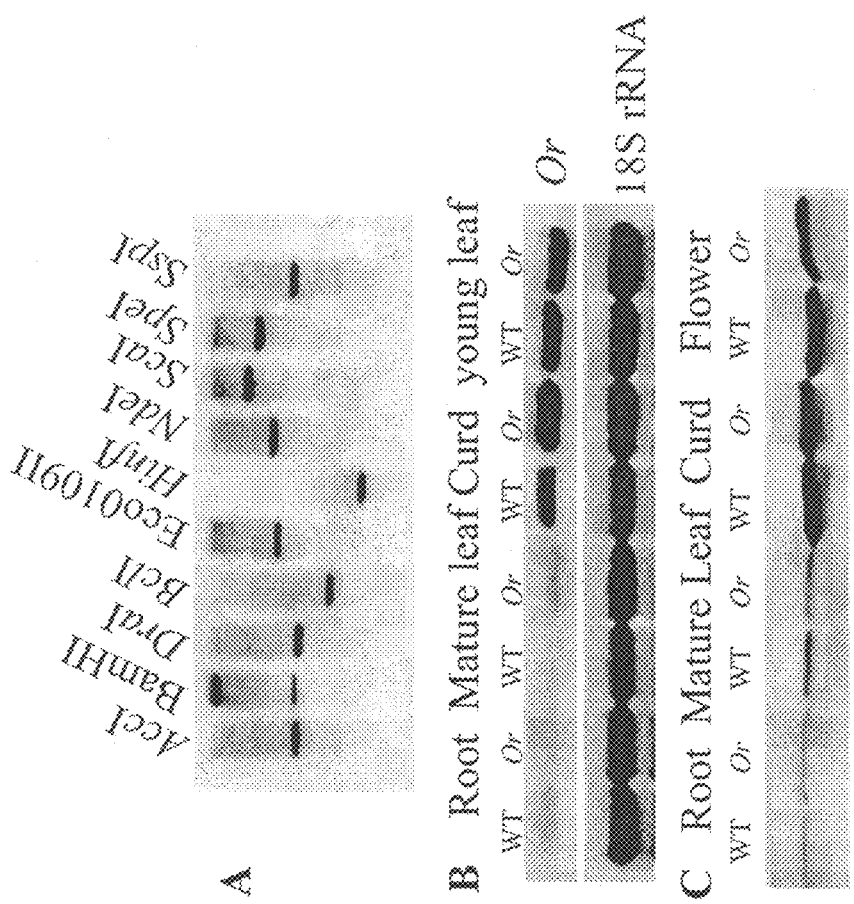
FIGS. 9A-C depict the molecular analysis of Or. Southern analysis (FIG. 9A) revealed that Or represents a single copy sequence in the cauliflower genome. Northern (FIG. 9B) and Western (FIG. 9C) analysis showed that Or is highly expressed in curds, flowers and young leaves at comparable levels between wild type and mutant.

Southern analysis revealed that the Or gene represented a single-copy sequence in the cauliflower genome (FIG. 9A). Northern blots probed with either the 5' or 3'end fragment of the Or gene showed no notable smaller or larger transcripts. The blots probed with the sequences flanking Or detected no bands. Due to the fact that the Or-D1 is the most abundant transcript and only small size difference exists between the Or variants and WT or transcript, we detected transcripts of a similar size for WT and mutant. A comparable abundance of transcripts was observed in the curds, flowers, and very young leaves of both the WT and the mutant (FIG. 9B). The amount observed in mature leaves and roots was much lower.

Example 7

Anti-Or Antibody Production

An antibody was produced which recognizes the C-terminal sequence of the Or protein, that portion of the protein shared by both WT and mutant. A truncated form of Or without putative transit peptide sequence was inserted into pET-32a vector (Novagen) and transformed into Rosetta2 DE3 cells (Novagen, Madison, Wis.) for high level of expression of Or protein. The expression was induced by 1 mM IPTG for 4 hours at 37° C. The recombinant protein was purified by affinity chromatography and used to immunize rabbits for raising polyclonal anti-Or antibody at Cornell Center for Animal Research and Education. Western analysis showed that the amounts of protein are much higher in curds and flowers than other tissues (FIG. 9C). The mature protein showed a size of approximately 28 kDa. Interestingly, the size of the mature WT and mutant protein was also shown to be similar. The putative protein encoded by Or-D2 could not be detected, even when a high percentage of acrylamide gel (15%) was utilized, suggesting that Or-D2 may not be translated or that the Or-D2 protein is not stable.

Example 8

Protein Gel Electrophoresis and Western Blotting Analysis

For SDS-PAGE gel electrophoresis, 50 mg of plant material was ground and extracted in 150 µl of 40% sucrose, 500 µl liquid phenol, 10 µl 10% SDS, and 20 µl beta-mercaptoethanol. After 5 minutes centrifugation at 10,000 g, 15 µl of the supernatant was mixed with same volume of 1% Fill 400, and 900 µl of methanol. The sample was mixed and then centrifuged at 10,000 for 10 minutes. The pellet was washed with methanol, redissolved in 50 µl of 1×SDS loading buffer, and loaded on 15% SDS-polyacrylamide gel (Sambrook et al. 1989, supra).

For Western blot analysis, proteins were blotted onto Protean Nitrocellulose Membrane (0.2 µm, Schleicher & Schuell) with a TE 70 Semi-Dry Transfer Unit (Amersham). Ponceau S staining of the transferred blot was used for monitoring transfer efficiency. A duplicate gel was run and stained by Coomassie Brilliant Blue R-250 for monitoring an equal loading of samples. For different plant materials, pre-immune serum was used to control for non-specific cross-reaction. Anti-Or serum was used at 1000× dilution, and HRP-conjugated goat-anti-rabbit IgG (Bio-Rad) was used at 2000× dilution. Immun-Star HRP substrate (Bio-Rad) was used in ECL detection. The signal was monitored by either exposing to X-ray film or being scanned by Storm 860 at wavelengths of 440 nm (absorption) and 560 nm (emission).

Example 9

Plastid Localization of the Or Protein

In plants, carotenoids are synthesized exclusively in plastids. The Or protein is predicted to have a plastid localization. To examine its subcellular localization in the plant, we have fused the entire coding region of the wild type or gene to a modified green fluorescent protein (GFP) gene under the control of 35S promoter (von Arnim et al. 1998. Gene 221: 35-43) and transformed the construct into Arabidopsis. In leaf tissue, the Or-GFP appeared not to express in the fully developed chloroplasts (data not shown), but expressed predominantly at epidermis cells in the leucoplasts (FIG. 10A), which are the main plastid found in WT cauliflower curds (Li et al. 2001, supra). The fluorescence of Or-GPF was also detected in the membrane of starch granules in the developing seeds (FIG. 10C and insert), concomitantly with 13-carotene accumulation in amylo-chromoplasts in pith tissue of cauliflower. Further, immunoblot analysis of proteins from the purified chromoplasts or leucoplasts demonstrated the association of Or protein with these plastids (data not shown). These results confirm the predicted plastid localization.

Example 10

Or Orthologs in Divergent Plant Species

Figure 11A:
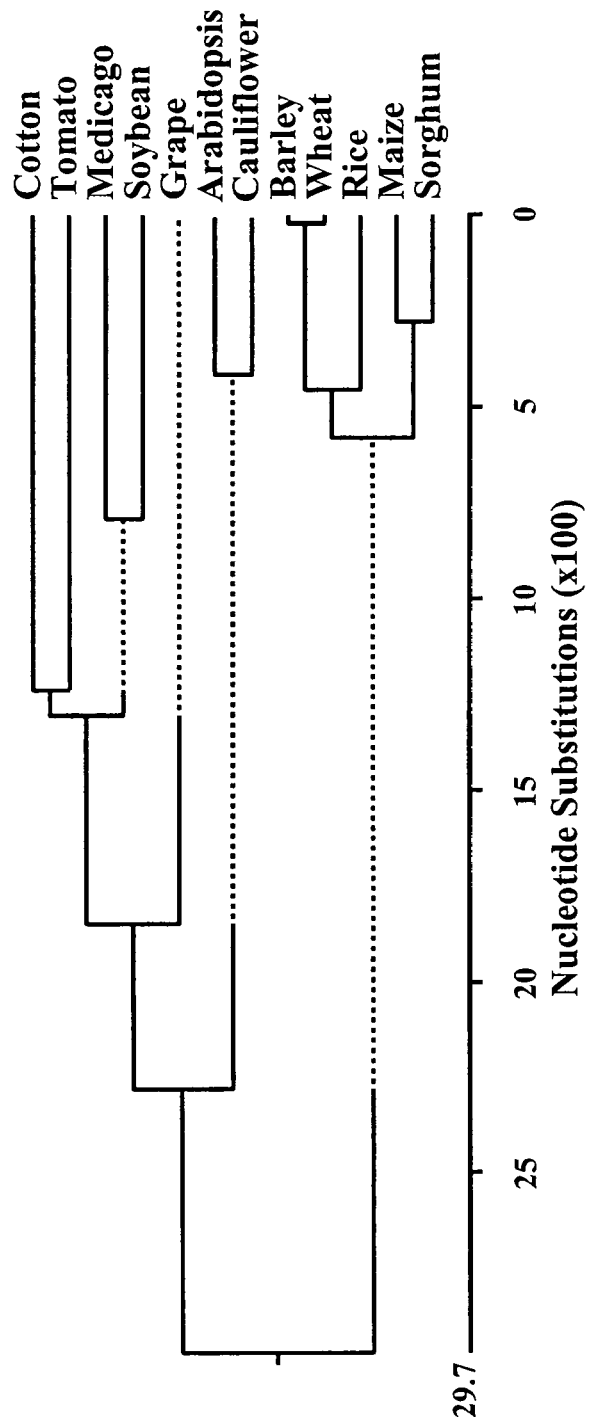
FIGS. 11A and B show the phylogenetic tree (FIG. 11A) and sequence alignment (FIG. 11B) showing high amino acid sequence similarity among different plant species. The bars show the transmembrane domains. The atypical DnaJ zinc figure motif with a 4 cysteine-rich repeat is indicated below the sequence.
Figure 11B:
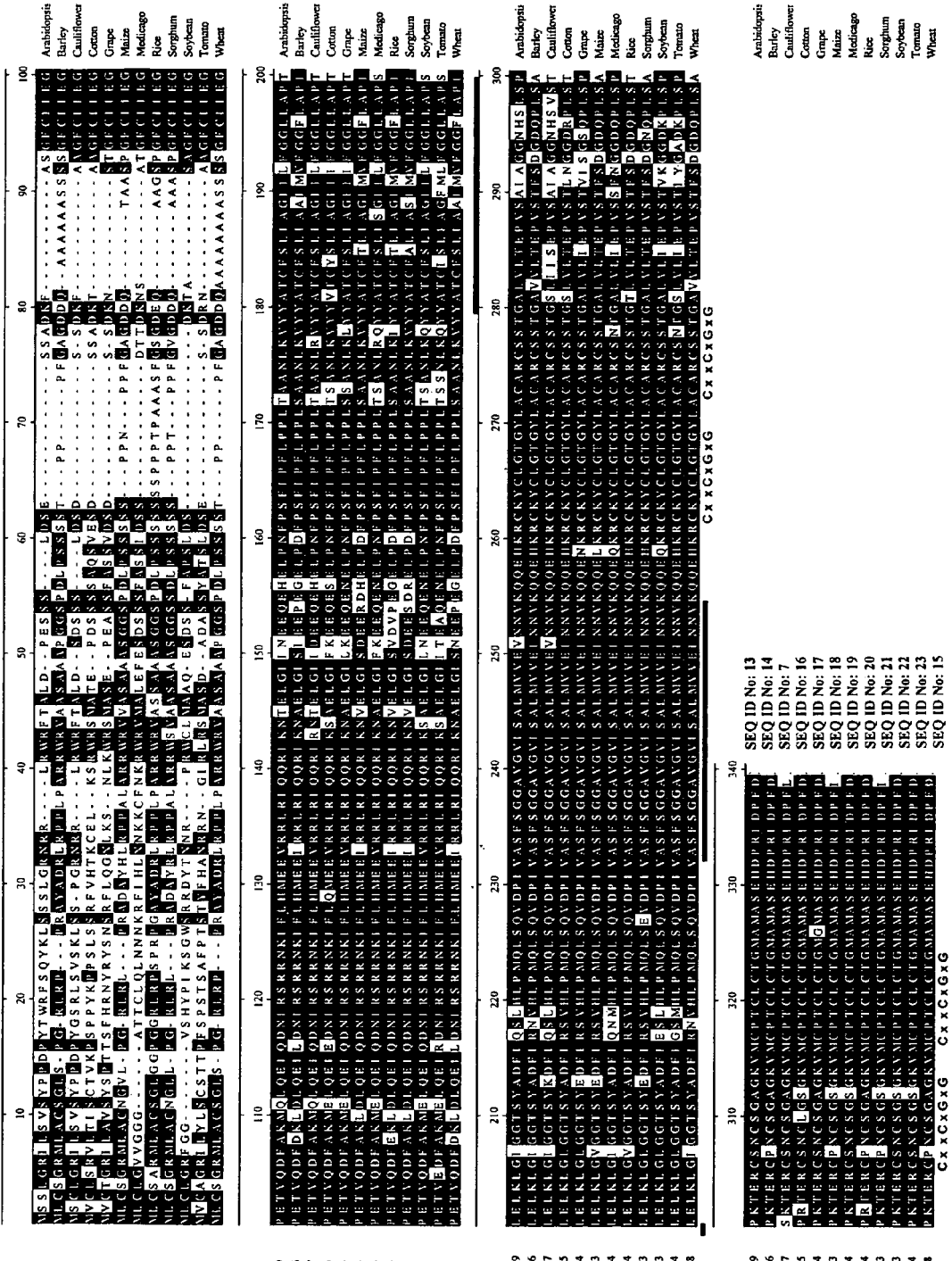

Homologs of the nucleotide sequence of Or are found in other higher plants utilizing search tools such as BLAST. Putative protein sequences were translated and aligned by ClastalW (Lasergene) to generate a phylogenetic tree (FIG. 11A) and sequence alignment showing high amino acid sequence similarity among different plant species (FIG.

11B). Orthologs with a high degree of sequence homology were found in many other plants including *Arabidopsis*, tomato, maize, and rice etc. Searching microarray expression profile databases revealed that the *Arabidopsis* Or ortholog expresses mainly in meristem tissues, and the tomato Or ortholog expresses in flowers and developing fruits, which agrees well with the general Or expression pattern in cauliflower.

To examine whether Or functions in another plant, we transformed the Or genomic fragment into *Arabidopsis* ap1-1/cal-1 "cauliflower" mutant (Bowman et al. 1993. *Development* 119: 721-743). Expression of the Or gene in the *Arabidopsis* mutant resulted in production of "orange-yellow" color instead of the normal pale green hue in the inflorescence meristems (FIG. 12A). HPLC analysis confirmed that the color shift is indeed associated with enhanced carotenoid accumulation (FIG. 12B). The total carotenoids in the inflorescence meristems increased 2-fold over the control, which is a significant increase in a green tissue background (FIG. 12C). Notably, the Or gene confers not only the increased accumulation of n-carotene, but also other carotenoids in *Arabidopsis*. The successful phenotypic complementation of Or in the *Arabidopsis* mutant provides strong evidence that Or can work across species to enhance carotenoid accumulation.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated genomic nucleic acid comprising the sequence set forth in SE) ID NO: 2.

2. The nucleic acid molecule according to claim 1, wherein the nucleotide sequence is optimized for expression in a plant.

3. A DNA construct comprising the nucleic acid molecule of claim 1, wherein said nucleotide sequence is linked to a promoter that drives expression in a host cell.

4. A vector comprising the nucleic acid of claim 1.

5. A host cell comprising the vector of claim 4.

6. The host cell of claim 5, wherein said host cell is a single-celled or lower or higher multi-celled organism into which the construct according to the invention can be introduced so as to produce an Or protein.

7. The host cell of claim 6, wherein said host cell is a plant cell.

8. The host cell of claim 6, wherein said host cell is a bacterial, a fungal or an algal cell.

9. A transgenic plant containing the nucleic acid sequence according to claim 1 or a progeny of said plant containing the nucleic acid sequence according to claim 1 wherein the level of carotenoid accumulation in said plant or progeny of said plant is altered when compared to plants of the same species which have not been transformed.

10. A transgenic plant in which the nucleic acid sequence according to claim 1 has been introduced or a progeny of said plant in which said nucleic acid sequence has been introduced in said progeny and in which the level of carotenoid accumulation in said plant or progeny of said plant is altered, or a tissue thereof.

11. A plant cell or plant part of the plant of claim 9 or 10.

12. The transgenic plant of claim 9 where the plant is a monocotyledonous plant.

13. The transgenic plant of claim 9 where the plant is a dicotyledonous plant.

14. A host cell having stably incorporated into its genome at least one DNA construct of claim 3.

15. The host cell of claim 14, wherein said host cell is a single-celled or lower or higher multi-celled organism into which the construct according to the invention can be introduced so as to produce an Or protein.

16. The host cell of claim 15, wherein said host cell is a plant cell.

17. The host cell of claim 16, wherein the plant cell is from a plant selected from the group consisting of cauliflower, *Arabidopsis*, barley, cotton, grape, maize, medicago, rice, soybean, tomato, and wheat.

18. The host cell of claim 16, wherein the plant cell is from a plant selected from the group consisting of *Arabidopsis, Brassica, Glycine, Gossypium, Hordeum, Lycopersicon, Medicago, Oryza, Sorghum, Triticum, Vitis*, and *Zea*.

19. The host cell of claim 15, wherein said host cell is a bacterial, a fungal or an algal cell.

20. A transformed plant produced by a method comprising: transforming a plant with the nucleic acid of claim 1.

21. A method of regulating accumulation of carotenoids in a plant comprising introducing the nucleic acid sequence according to claim 1 into a plant or plant cells and then allowing said nucleic acid sequence to be expressed in said plant or plant cells.

22. The method for regulating accumulation of carotenoids in a plant cell according to claim 21 wherein the plant cell is a cell of cauliflower, *Arabidopsis*, barley, cotton, grape, maize, medicago, rice, soybean, tomato, and wheat.

* * * * *